(12) United States Patent
Or et al.

(10) Patent No.: US 10,323,060 B2
(45) Date of Patent: Jun. 18, 2019

(54) BENZOIC ACID DERIVATIVES OF BILE ACID AS FXR/TGR5 AGONISTS AND METHODS OF USE THEREOF

(71) Applicant: ENANTA PHARMACEUTICALS, INC., Watertown, MA (US)

(72) Inventors: Yat Sun Or, Watertown, MA (US); Xuechao Xing, Wilmington, MA (US); Guoqiang Wang, Belmont, MA (US); Ruichao Shen, West Roxbury, MA (US); Jing He, Somerville, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 15/439,303

(22) Filed: Feb. 22, 2017

(65) Prior Publication Data

US 2017/0240586 A1    Aug. 24, 2017

Related U.S. Application Data

(60) Provisional application No. 62/298,705, filed on Feb. 23, 2016.

(51) Int. Cl.
| | | |
|---|---|---|
| A61K 31/575 | (2006.01) |
| A61K 31/58 | (2006.01) |
| C07J 9/00 | (2006.01) |
| C07J 43/00 | (2006.01) |

(52) U.S. Cl.
CPC ............. *C07J 43/003* (2013.01); *C07J 9/00* (2013.01); *C07J 9/005* (2013.01)

(58) Field of Classification Search
CPC ............ C07J 9/00; C07J 9/005; C07J 43/003
USPC .......... 552/551, 553, 554; 514/172, 176, 182
See application file for complete search history.

(56) References Cited

U.S. PATENT DOCUMENTS

| 4,202,876 A | 5/1980 | Monks et al. |
|---|---|---|
| 5,466,815 A | 11/1995 | Enhsen et al. |
| 5,512,558 A | 4/1996 | Enhsen et al. |
| 5,646,316 A | 7/1997 | Jacobson et al. |
| 5,656,277 A | 8/1997 | Berlati et al. |
| 2005/0054559 A1 | 3/2005 | Gallop et al. |
| 2007/0142340 A1 | 6/2007 | Pellicciari |
| 2008/0039435 A1 | 2/2008 | Pellicciari |
| 2008/0182832 A1 | 7/2008 | Pellicciari et al. |
| 2008/0214515 A1 | 9/2008 | Ferrari et al. |
| 2009/0062526 A1 | 3/2009 | Yu et al. |
| 2009/0163474 A1 | 6/2009 | Zhang et al. |
| 2010/0063018 A1 | 3/2010 | Pellicciari et al. |
| 2010/0324004 A1 | 12/2010 | McLane et al. |
| 2011/0172198 A1 | 7/2011 | Pellicciari |
| 2013/0116218 A1 | 5/2013 | Kaplan et al. |
| 2013/0345188 A1 | 12/2013 | Steiner et al. |
| 2014/0057886 A1 | 2/2014 | Pellicciari et al. |
| 2014/0186438 A1 | 7/2014 | Manku et al. |
| 2014/0187633 A1 | 7/2014 | Manku et al. |
| 2014/0206657 A1 | 7/2014 | Yu et al. |
| 2014/0371190 A1 | 12/2014 | Pellicciari et al. |
| 2015/0112089 A1 | 4/2015 | Finch et al. |
| 2016/0130297 A1 | 5/2016 | Or et al. |
| 2016/0145295 A1 | 5/2016 | Or et al. |
| 2016/0145296 A1 | 5/2016 | Or et al. |
| 2016/0176917 A1 | 6/2016 | Wang et al. |
| 2016/0185815 A1 | 6/2016 | Wang et al. |
| 2016/0229886 A1 | 8/2016 | Shen et al. |
| 2016/0289262 A1 | 10/2016 | Wang et al. |
| 2017/0101434 A1 | 4/2017 | Pellicciari et al. |
| 2017/0260225 A1 | 9/2017 | Pellicciari et al. |
| 2018/0148469 A1 | 5/2018 | Wang et al. |
| 2018/0148470 A1 | 5/2018 | Li et al. |
| 2018/0237471 A1 | 8/2018 | Wang et al. |

FOREIGN PATENT DOCUMENTS

| CN | 105175473 A | 12/2015 |
|---|---|---|
| CN | 106478759 A | 3/2017 |
| CN | 106518946 A | 3/2017 |

(Continued)

OTHER PUBLICATIONS

Mayorquin-Torres et al., "Application of palladium-catalyzed carboxyl anhydride-boronic acid cross coupling in the synthesis of novel bile acids analogs with modified side chains". Steroids, vol. 101, pp. 21-27 (Year: 2015).*
U.S. Appl. No. 15/439,531, filed Feb. 22, 2017.
U.S. Appl. No. 15/439,358, filed Feb. 22, 2017.
Macchiarulo, et al., "Probing the Binding Site of Bile Acids in TGR5," Medicinal Chemistry Letters, 4(12):1158-1162, 2011.
Sato, et al., "Novel Potent and Selective Bile Acid Derivatives as TGR5 Agonists: Biological Screening, Structure-Activity Relationships, and Molecular Modeling Studies," J. Med. Chem., 51:1831-1841, 2008.

(Continued)

*Primary Examiner* — Barbara P Badio
(74) *Attorney, Agent, or Firm* — Edgar W. Harlan; Carolyn S. Elmore, Esq.; Elmore Patent Law Group, P.C.

(57) ABSTRACT

The present invention provides compounds of Formula I:

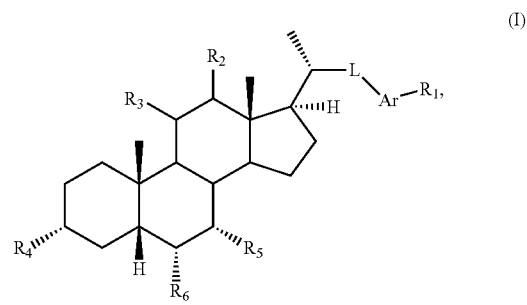

pharmaceutical compositions comprising these compounds and methods of using these compounds to treat or prevent a disease or disorder mediated by FXR and/or TGR5.

12 Claims, No Drawings

(56) References Cited

FOREIGN PATENT DOCUMENTS

| | | | |
|---|---|---|---|
| EP | 583566 | * | 2/1994 |
| EP | 1364645 | | 11/2003 |
| EP | 1947108 | A1 | 7/2008 |
| JP | H1160594 | A | 3/1999 |
| JP | H11109628 | A | 4/1999 |
| WO | 198702367 | A2 | 4/1987 |
| WO | 0037077 | A1 | 6/2000 |
| WO | 0228881 | A1 | 4/2002 |
| WO | 2003030612 | A2 | 4/2003 |
| WO | 2005089316 | A2 | 9/2005 |
| WO | 2007089907 | A2 | 8/2007 |
| WO | 2007111994 | A2 | 10/2007 |
| WO | 2008009407 | A2 | 1/2008 |
| WO | 2008091540 | A2 | 7/2008 |
| WO | 2010014836 | A3 | 2/2010 |
| WO | 2013020108 | A2 | 2/2013 |
| WO | 2013166176 | A1 | 11/2013 |
| WO | 2013192097 | A1 | 12/2013 |
| WO | 2014036379 | A2 | 3/2014 |
| WO | 2014184271 | A1 | 11/2014 |
| WO | 2015017813 | A2 | 2/2015 |
| WO | 2015181275 | A1 | 12/2015 |
| WO | 2016173493 | A2 | 11/2016 |
| WO | 2016173524 | A1 | 11/2016 |
| WO | 2016205475 | A | 12/2016 |
| WO | 2017027396 | A1 | 2/2017 |
| WO | 2017053826 | A1 | 3/2017 |
| WO | 2017129125 | A3 | 8/2017 |

OTHER PUBLICATIONS

Mosesin-4' at www.chemspider.com/ Chemical-Structure.10375019.html (retrieved from the internet Oct. 11, 2016).
Pellicciari, et al., "6α-Ethyl-Chenodeoxycholic Acid (6-ECDCA), a Potent and Selective FXR Agonist Endowed with Anticholestatic Activity," Journal of Medicinal Chemistry, 45(17):3569-3572, 2002.
Silverman, "Prodrugs and Drug Delivery Systems," The Organic Chemistry of Drug Design and Drug Action, pp. 352-399, 1992.
Banker, et al., Modern Pharmaceutics, 3rd edition, 1996.
Bundgaard, "Design of Prodrugs: Bioreversible derivatives for various functional groups and chemical entities," Design of Prodrugs, Chapter 1, 1985.
Wolff, Burger's Medicinal Chemistry and Drug Discovery, 5(1):975-977, 1995.
Kim, et al., "Synthesis and Antimicrobial Activity of New 3α-Hydroxy-23,24-bisnorcholane Polyamine Carbamates," Bioorganic & Medicinal Chemistry Letters, 11:3065-3068, 2001.
Solaja, et al., "Novel 4-Aminoquinolines Active against Chloroquine-Resistant and Sensitive P. falciparum Strains that also Inhibit Botulinum Serotype A," J. Med. Chem., 51:4388-4391, 2008.
Willemen, et al., "Alkyl Derivatives of Cholic Acid as Organogelators: One-Component and Two-Component Gels," Langmuir, 18(19):7102-7106, 2002.
Pore, et al., "Design and synthesis of fluconazole/bile acid conjugate using click reaction", Tetrahedron, 62:11178-11186, 2006.
Nikolaienko, et al., "Rapid way to fluorescent cholic-based chemosensor precursors", Synthetic Organic Chemistry, pp. 1-4, 2011.
Sepe, et al., "Farnesoid X receptor modulators (2011-2014): a patent review," Expert Opinion on Therapeutic Patents, 25:8, 885-896, 2015.
U.S. Appl. No. 15/826,233, filed Nov. 29, 2017.
Crawley, "Farnesoid X Receptor Modulators: a patent review," Expert Opinion on Therapeutic Patents, 20(8): 1047-1057, 2010.

Ballatore, C., et al., "Carboxylic Acid (Bio)Isosteres in Drug Design," ChemMedChem., (8)3: 385-395, 2013.
Briere, et al., "Novel small molecule agonist of TGR5 possesses anti-diabetic effects but causes gallbladder filling in mice." PLOS one, 10(8):1-17, 2015.
Okahata, et al., "Catalytic Hydrolysis of p-Nitrophenyl Esters in the Presence of Representative Ammonium Aggregates. Specific Activation of a Cholesteryl Nucleophile Bound to a Dialkylammonium Bilayer Membrane." Bulletin of hte Chemical Society of Japan, 52(12):3647-3653, 1979.
Sajisha, et al., "Remarkable isomer-selective gelation of aromatic solvents by a polymorph of a urea-linked bile acid-amino acid conjugate," RSC Advances, 4(81):43167-43171, 2014. Abstract only.
Ali, et al., "Recent advances in the development of farnesoid X receptor agonists," Ann Transl Med, 3(1):5, pp. 1-16, 2015.
PUBCHEM-CID-122592927, Created Date: Dec. 8, 2016.
PUBCHEM-CID-122592945, Created Date: Dec. 8, 2016.
Pellicciari, R., et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", Journal of Medicinal Chemistry, American Chemical Society, 47:4559-4569, 2004.
Okahata, Y., et al., "Base-catalyzed proton abstraction from .beta.-(p-nitrophenoxy)propiophenone in the presence of single-chain, double-chain, and triple-chain ammonium bilayer membrane aggregates", Database CA [Online] Chemical Abstracts Service, Database accession No. 1980:549272, abstract, 1980.
U.S. Appl. No. 15/948,370, filed Apr. 9, 2018.
Pellicciari, et al. "Back Door Modulation of the Farnesoid X Receptor: Design, Synthesis and Biological Evaluation of a Series of Side Chain Modified Chenodeoxycholic Acid Derivatives", Journal of Medicinal Chemi, American Chemical Society, 49:4208-4215, 2006.
Honorio, K. M., et al., "Hologram QSAR Studies on Farnesoid X Receptor Activators," Letters in Drug Design & Discovery, (3):261-267, 2006.
Gioiello Antimo, et al., "Extending SAR of bile acids as FXR ligands: discovery of 23-N-(carbocinnamyloxy)-3[alpha],7[alpha]dihydroxy-6[alpha]-ethyl-24-nor-5[beta]-cholan-23-amine", Bioorganic & Medicinal Chemistry, 19(8):2650-2658, 2011.
Griffiths, et al., "Charge-remote fragmentation of bile acids derivatized with amino-sulphonic acids," Rapid Communication in Mass Spectrometry, 7(3):235-240, 1993.
Coleman, J. P., et al., "Metabolic Fate and Hepatocyte Toxicity of Reverse Amide Analogs of Conjugated Ursodeoxycholate in the Rat," J. Steroid Biochem. Molec. Biol., 64(1/2): 91-101, 1998.
Opsenica, I. M., et al., "4-Amino-7-chloroquinolines: Probing Ligand Efficiency Provides Botulinum Neurotoxin Serotype A Light Chain Inhibitors with Significant Antiprotozoal Activity," J. Med. Chem., (56):5860-5871, 2013.
Fini, A., et al. "Basic Cholane Derivatives. XI: Comparison between Acid and Basic Derivatives," Journal of Pharmaceutical Sciences, (81)7:726-730, 1992.
Fini, A., et al., "Quantitative Structure-Antimicrobial Activity Relationship in 5B-Cholanyl-24-benzylamine Derivatives," Journal of Pharmaceutical Sciences, (79)7:603-605, 1990.
Okada, J. , "Preparation of bile acid derivatives and their use as nasal absorption enhancers", Database CA [Online] Chemical Abstracts Service, Columbus, Ohio, US; retrieved from STN Database accession No. 1999:142390.
Roda, A. et al., "Effect of Basic Cholane Derivatives on Intestinal Cholic Acid Metabolism: In Vitro and In Vivo Activity", Journal of Pharmaceutical Sciences, vol. 81, No. 3, 1992, 237-240.

* cited by examiner

BENZOIC ACID DERIVATIVES OF BILE ACID AS FXR/TGR5 AGONISTS AND METHODS OF USE THEREOF

RELATED APPLICATION

This application claims the benefit of U.S. Provisional Application No. 62/298,705, filed on Feb. 23, 2016. The entire teachings of the above application are incorporated herein by reference.

TECHNICAL FIELD

The present invention relates generally to compounds and pharmaceutical compositions useful as FXR/TGR5 modulators. Specifically, the present invention relates to bile acid derivatives and methods for their preparation and use.

BACKGROUND OF THE INVENTION

Farnesoid X Receptor (FXR) is an orphan nuclear receptor initially identified from a rat liver cDNA library (BM. Forman, et al., *Cell,* 1995, 81(5), 687-693) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., *Cell,* 1995, 83(6), 841-850). The relevant physiological ligands of FXR are bile acids (D. Parks et al., *Science,* 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., *Genes Dev.,* 2003, 17(13), 1581-1591; T. Inagaki et al., *Cell Metab.,* 2005, 2(4), 217-225).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, and WO 2008/025540. Further small molecule FXR modulators have been recently reviewed (R. C. Buijsman et al. *Curr. Med. Chem.* 2005, 12, 1017-1075).

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm (Kawamata et al., *J. Bio. Chem.,* 2003, 278, 9435). TGR5 has been found to be identical to hGPCR19 reported by Takeda et al., *FEBS Lett.* 2002, 520, 97-101.

TGR5 is associated with the intracellular accumulation of cAMP, which is widely expressed in diverse cell types. While the activation of this membrane receptor in macrophages decreases pro-inflammatory cytokine production, (Kawamata, Y., et al., *J. Biol. Chem.* 2003, 278, 9435-9440) the stimulation of TGR5 by BAs in adipocytes and myocytes enhances energy expenditure (Watanabe, M., et al. Nature. 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T., et al., *J. Endocrinol.* 2006, 191, 197-205). In addition, and in line with the involvement of TGR5 in energy homeostasis, bile acid activation of the membrane receptor has also been reported to promote the production of glucagon-like peptide 1 (GLP-1) in murine enteroendocrine cell lines (Katsuma, S., *Biochem. Biophys. Res. Commun.,* 2005, 329, 386-390). On the basis of all the above observations, TGR5 is an attractive target for the treatment of disease e.g., obesity, diabetes and metabolic syndrome.

In addition to the use of TGR5 agonists for the treatment and prevention of metabolic diseases, compounds that modulate TGR5 modulators are also useful for the treatment of other diseases e.g., central nervous diseases as well as inflammatory diseases (WO 01/77325 and WO 02/84286). Modulators of TGR5 also provide methods of regulating bile acid and cholesterol homeostasis, fatty acid absorption, and protein and carbohydrate digestion.

There is a need for the development of FXR and/or TGR5 modulators for the treatment and prevention of disease.

SUMMARY OF THE INVENTION

In one aspect, the invention provides compounds represented by Formula (I), or pharmaceutically acceptable salts, stereoisomer, solvate, hydrate or combination thereof:

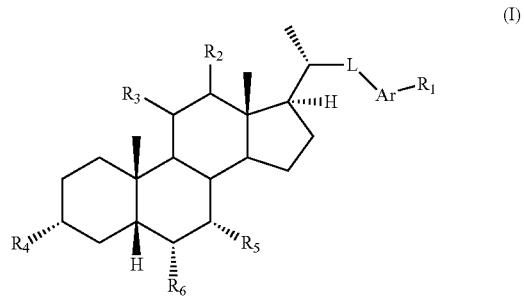

wherein:
$R_1$ is hydrogen, —C(O)$R_{11}$; —C(O)N$R_{12}R_{13}$, —C(O)NHSO$_2R_{11}$, —P(O)($R_{11})_2$, —CN, or tetrazolyl; Ar is optionally substituted aryl or optionally substituted heteroaryl; preferably, Ar is phenyl, pyridyl, pyrimidyl, pyrazinyl, pyridazinyl, triazinyl, tetrazinyl, tetrazolyl, indolyl, indazolyl, thienyl, benzothienyl, furanyl, benzofuranyl, isoxazolyl, benzoxazolyl, thiazolyl, benzothiazolyl, benzotriazolyl, imidazolyl, or benzoimidazolyl, each of which is optionally substituted;

L is selected from the group consisting of:
1) Substituted or unsubstituted —$C_1$-$C_8$-alkylene;
2) Substituted or unsubstituted —$C_2$-$C_8$-alkenylene;
3) Substituted or unsubstituted —$C_2$-$C_8$-alkynylene;
4) Substituted or unsubstituted —$C_3$-$C_8$-cycloalkylene;
5) Substituted or unsubstituted —$C_1$-$C_7$ alkoxylene;
6) Substituted or unsubstituted —$C_1$-$C_7$ aminoalkylene;
7) Substituted or unsubstituted —$C_3$-$C_7$ heterocycloalkylene;
8) Substituted or unsubstituted —$C_1$-$C_8$-alkylene-$C_3$-$C_8$-cycloalkylene;
9) Substituted or unsubstituted —$C_1$-$C_8$-alkylene-$C_3$-$C_7$-heterocycloalkylene;
10) Substituted or unsubstituted alkylaryl;
11) Substituted or unsubstituted alkylheteroaryl;

$R_2$ is hydrogen, hydroxyl, halogen, —$OSO_3H$, —$OSO_3$—, —OAc, —$OPO_3H_2$ or —$OPO_3^{2-}$; preferably $R_2$ is hydrogen or hydroxyl;

$R_3$ is hydrogen, halogen, CN, $N_3$, hydroxyl, —$OSO_3H$, —$OSO_3$, —OAc, —$OPO_3H_2$, —$OPO_3^{2-}$, —$SR_{12}$ or —$NHR_{12}$; preferably $R_3$ is hydrogen;

alternatively, $R_2$ and $R_3$ are taken together with the carbon atoms to which they are attached to form —CH═CH— or cycloalkyl ring or heterocycloalkyl ring such as, but not limited to cyclopropyl, or epoxide;

$R_4$ and $R_5$ are each independently selected from hydrogen or hydroxyl protecting group such as, but not limited to acetyl, trimethyl silyl, t-Butyldimethylsilyl, or benzyl; preferably $R_4$ and $R_5$ are hydrogen;

$R_6$ is selected from the group consisting of:
1) Hydrogen;
2) Halogen;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted —$C_1$-$C_7$ alkoxyl;
8) Substituted or unsubstituted —$C_1$-$C_7$ aminoalkyl;
9) Substituted or unsubstituted —$C_3$-$C_7$ heterocycloalkyl;
preferably $R_6$ is $C_1$-$C_4$-alkyl, more preferably $R_6$ is ethyl;

$R_{11}$ at each occurrence is independently selected from the group consisting of:
1) Hydrogen;
2) Halogen;
3) Hydroxyl;
4) Substituted or unsubstituted —$C_1$-$C_8$ alkoxy;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted —$C_3$-$C_8$ cycloalkenyl;
10) Substituted or unsubstituted 3- to 8-membered heterocycloalkyl;
11) Substituted or unsubstituted aryl;
12) Substituted or unsubstituted arylalkyl;
13) Substituted or unsubstituted heteroaryl; and
14) Substituted or unsubstituted heteroarylalkyl; and $R_{12}$ and $R_{13}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; preferably $R_{12}$ is optionally substituted —$C_1$-$C_8$ alkyl or optionally substituted aryl; alternatively, $R_{12}$ and $R_{13}$ are taken together with the nitrogen atom to which they are attached to form an optionally substituted heterocyclic ring.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of formula (I). The present invention also provides the use of a compound of formula (I) for the preparation of a medicament for the prevention or treatment of an FXR mediated disease or condition.

In yet another embodiment, the present invention provides a method for the prevention or treatment of a TGR5 mediated disease or condition. The method comprises administering a therapeutically effective amount of a compound of formula (I). The present invention also provides the use of a compound of formula (I) for the preparation of a medicament for the prevention or treatment of a TGR5 mediated disease or condition.

In certain embodiments, a disease that involves modulation of the TGR5 receptor is selected from metabolic disease, inflammatory disease, liver disease, autoimmune disease, cardiac disease, kidney disease, cancer, and gastrointestinal disease.

DETAILED DESCRIPTION OF THE INVENTION

A first embodiment of the invention is a compound represented by Formula I as described above, or a pharmaceutically acceptable salt, hydrate, solvate, ester or prodrug thereof.

In preferred embodiments, the compounds of the invention have the stereochemistry set forth in Formula Ia:

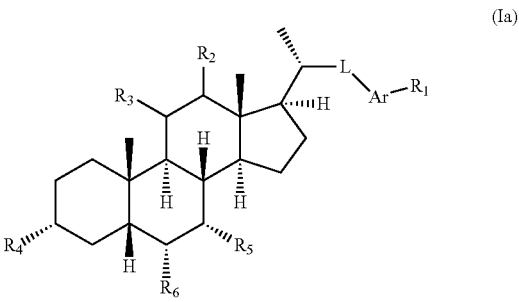

(Ia)

wherein Ar, L, and $R_1$-$R_6$ are as previously defined.

A second embodiment of the invention is a compound represented by Formula II or a pharmaceutically acceptable salt, hydrate, solvate, ester or prodrug thereof:

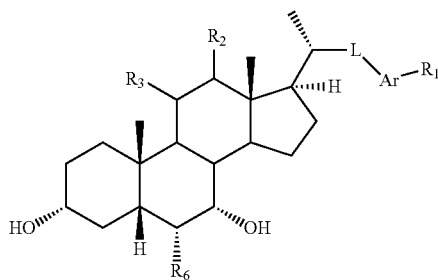
(II)

wherein $R_1$, Ar, L, $R_2$, $R_3$, and $R_6$ are as previously defined.

A third embodiment of the invention is a compound represented by Formula III or a pharmaceutically acceptable salt, hydrate, solvate, ester or prodrug thereof:

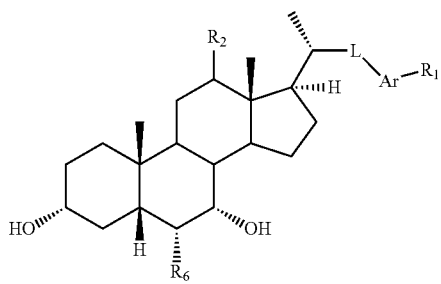
(III)

wherein $R_1$, Ar, L, $R_2$, and $R_6$ are as previously defined.

A Fourth embodiment of the invention is a compound represented by Formula IV or a pharmaceutically acceptable salt, solvate, hydrate, ester or prodrug thereof:

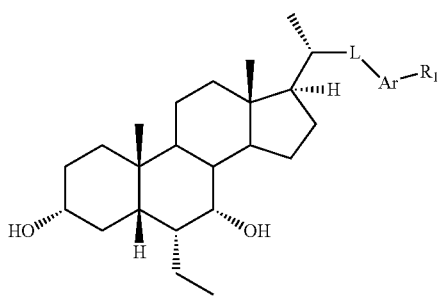
(IV)

wherein $R_1$, Ar and L are as previously defined.

In certain embodiments, the present invention relates to compounds of Formula (I), and pharmaceutically acceptable salts, solvates, hydrates, esters and prodrugs thereof, wherein —Ar—$R_1$ is selected from the groups set forth below, and can optionally be substituted when possible:

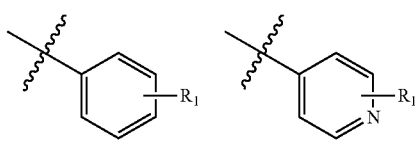

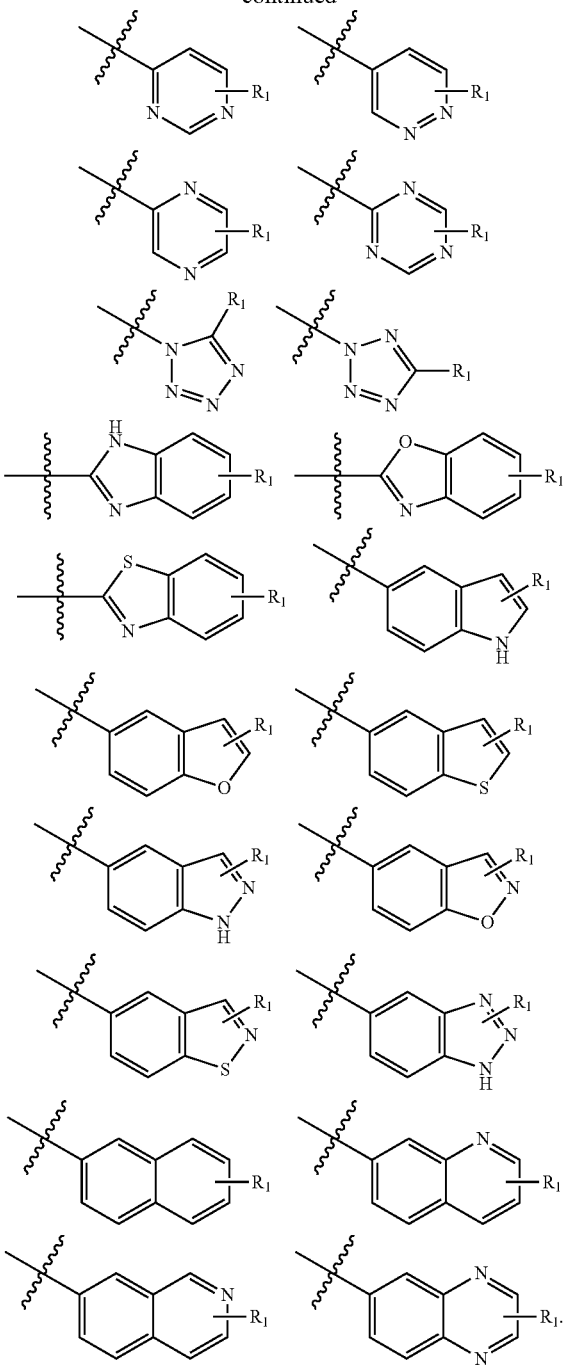

In certain embodiments of the compounds of the invention, $R_1$ is —$CO_2H$, —$CO_2Me$, —$CO_2Et$, or tetrazolyl.

In certain embodiments of the compounds of the invention, —Ar—$R_1$ is selected from the group below:

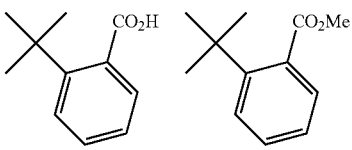

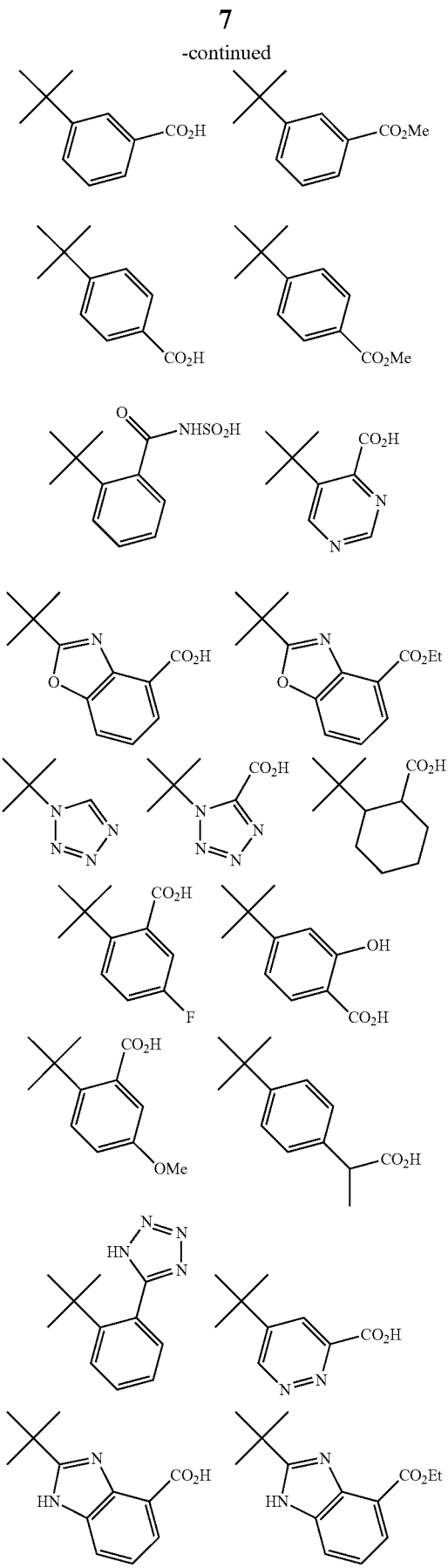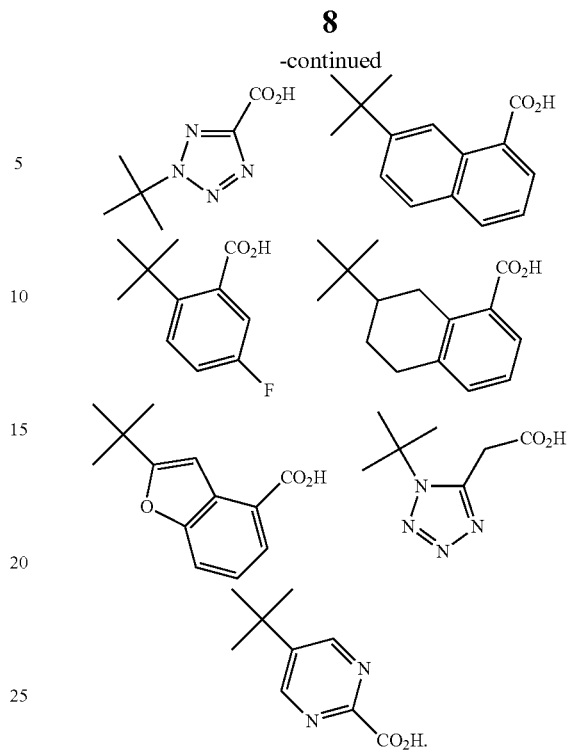
In certain embodiments of the compounds of the invention L is selected from the groups set forth below, and can optionally be substituted when possible:
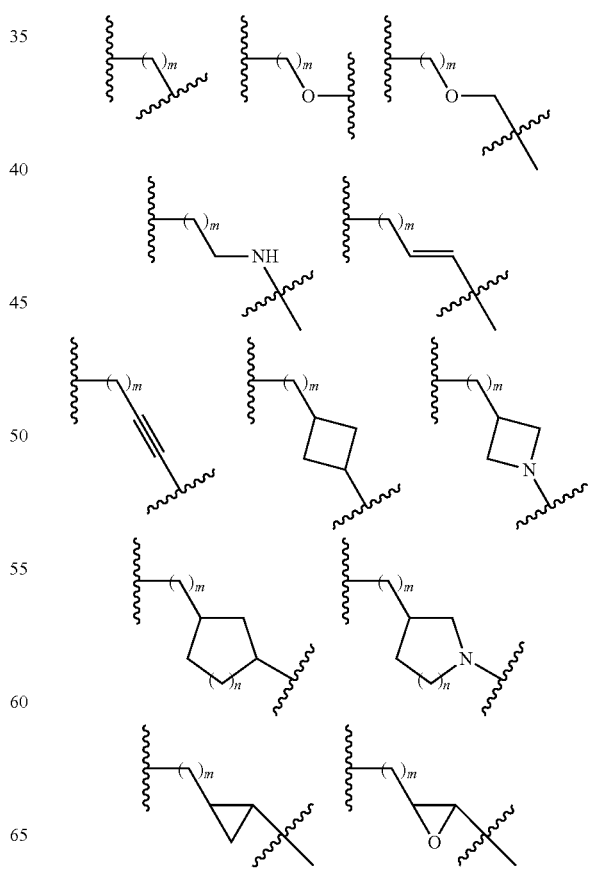

-continued

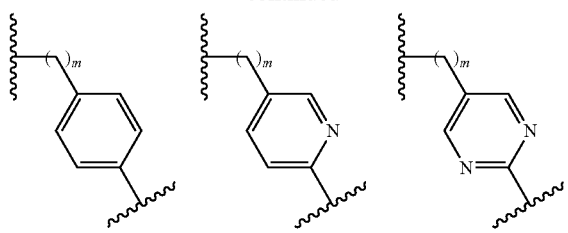

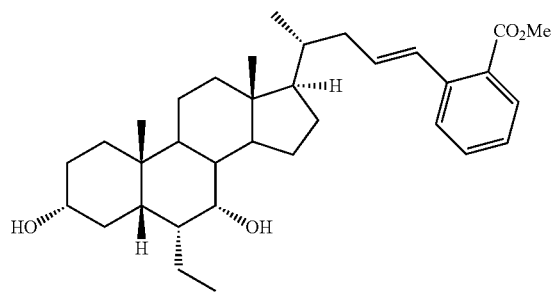
Compound 2

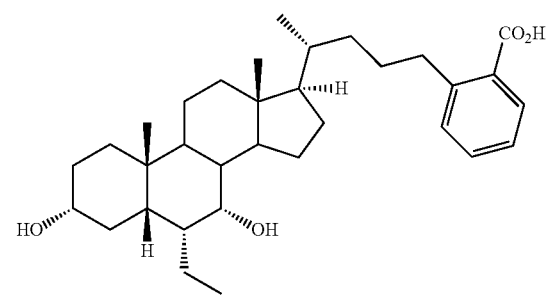
Compound 3 wherein m is 1, 2, 3, 4, 5, 6, or 7; n is 1, 2, or 3; preferably, when present, the optional substituent is OH, halogen, alkyl, alkoxyl, aryl or $CF_3$.

The compounds of the invention in certain embodiments do not include compounds of Formula I where L is $C_1$-$C_4$-alkylene and Ar is a five-membered heteroaryl group comprising three heteroatoms selected from oxygen, sulfur and nitrogen, such as 1,2,3-triazolyl; 1,3,4-triazolyl; 1,2,3-oxadiazolyl; 1,3,4-oxadiazolyl; 1, 2, 4-oxadiazolyl; 1,2,3-thiadiazolyl; 1,3,4-thiadiazolyl; or 1,2,4-thiadiazolyl.

The compounds of the invention in certain embodiments do not include compounds of Formula I where L is $C_1$-$C_4$-alkylheteroaryl and heteroaryl is a five-membered heteroaryl group comprising three heteroatoms selected from oxygen, sulfur and nitrogen, such as 1,2,3-triazolyl; 1,3,4-triazolyl; 1,2,3-oxadiazolyl; 1,3,4-oxadiazolyl; 1, 2, 4-oxadiazolyl; 1,2,3-thiadiazolyl; 1,3,4-thiadiazolyl; or 1,2,4-thiadiazolyl.

In another embodiment in combination with any of the above or below embodiments, the compounds of the invention according to Formulas (I)-(IV) include, but are not limited to, the following compounds 1 to 42, and pharmaceutically acceptable salts, prodrugs and solvates thereof:

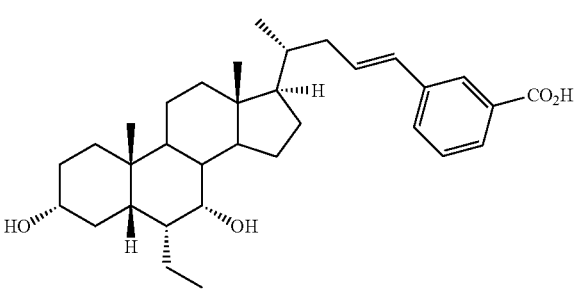
Compound 4

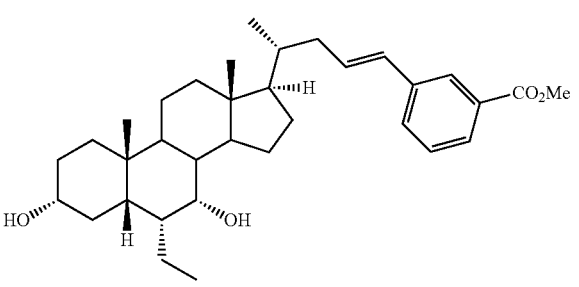
Compound 5

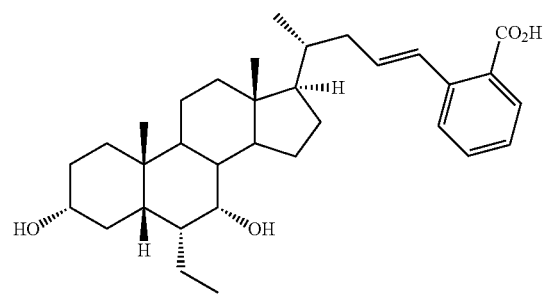
Compound 1

Compound 6

Compound 7
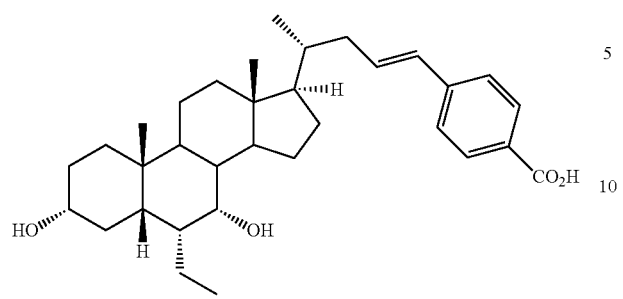
Compound 8
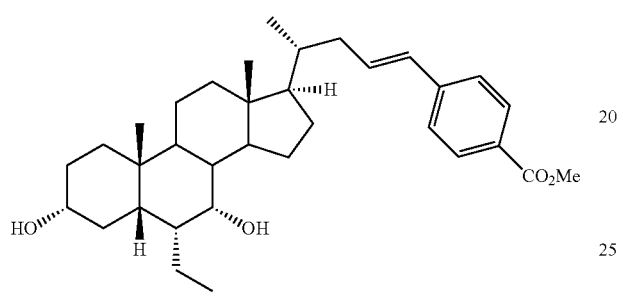
Compound 9
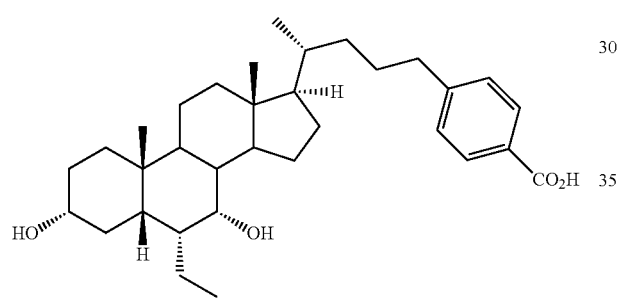
Compound 10
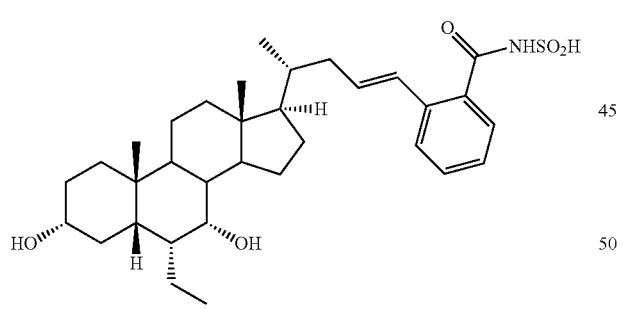
Compound 11
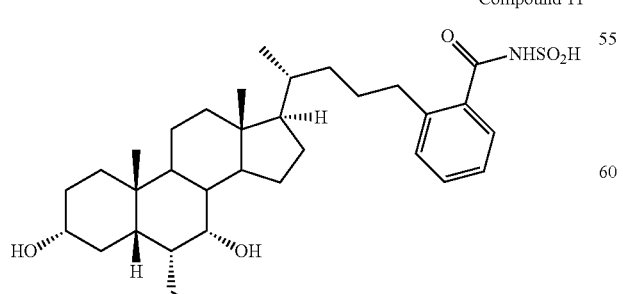
Compound 12
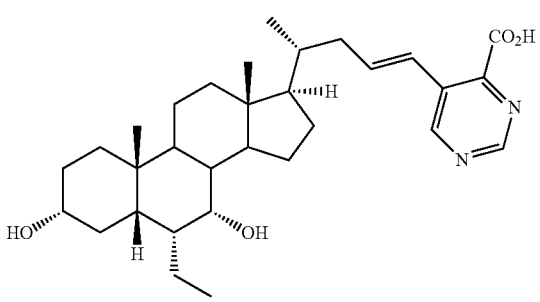
Compound 13
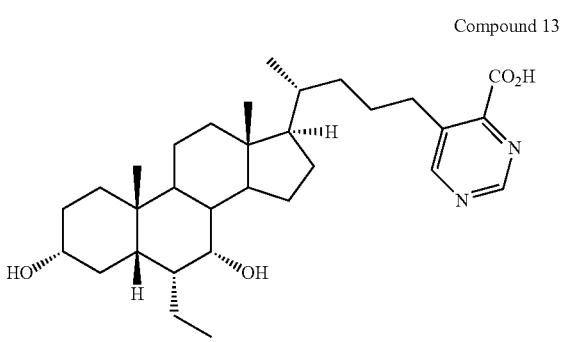
Compound 14
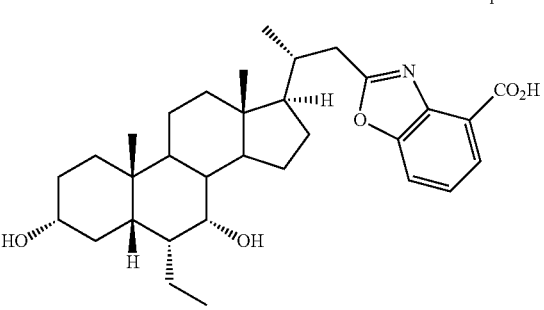
Compound 15
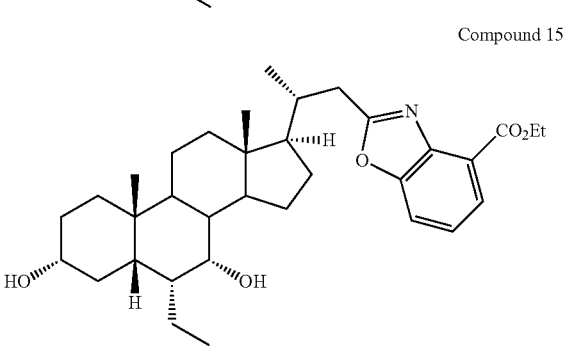
Compound 16
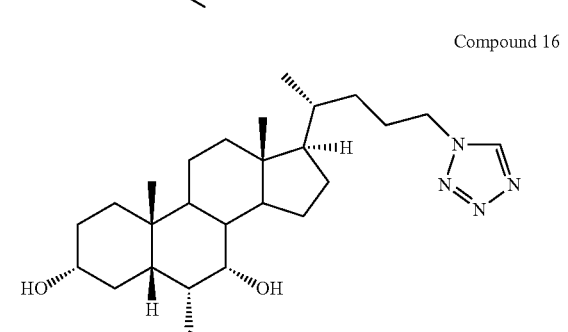

-continued
Compound 17
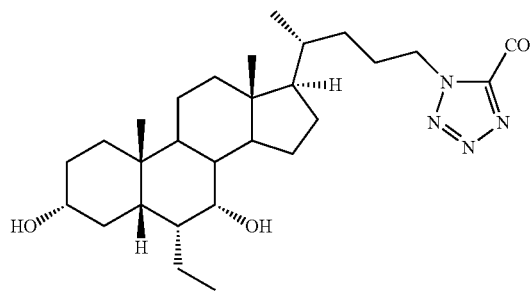
Compound 18
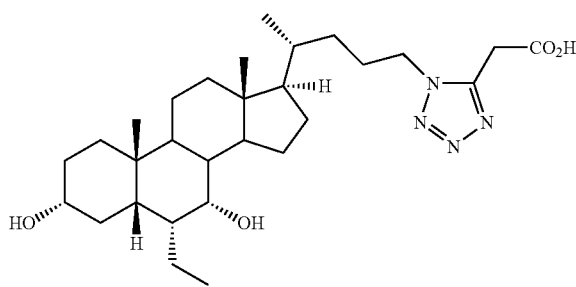
Compound 19
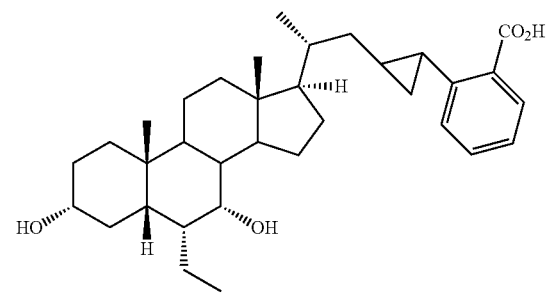
Compound 20
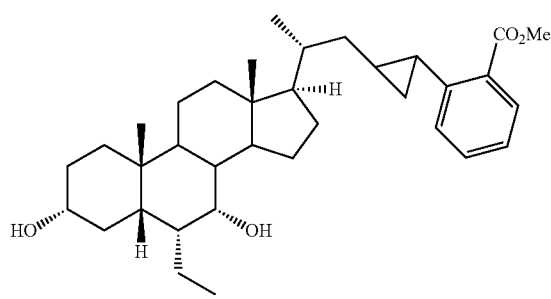
Compound 21
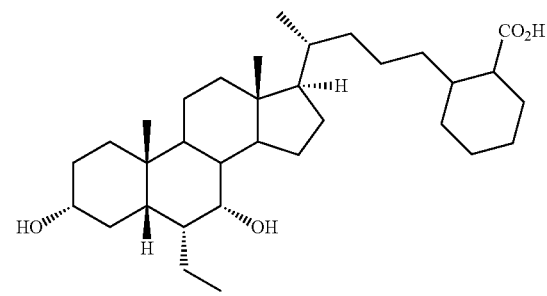
-continued
Compound 22
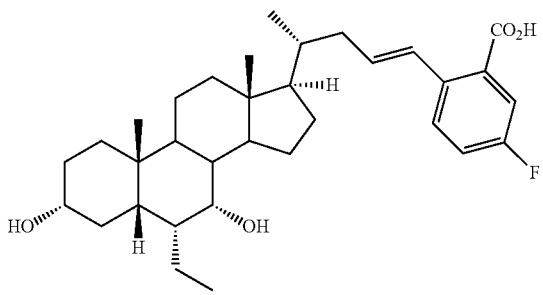
Compound 23
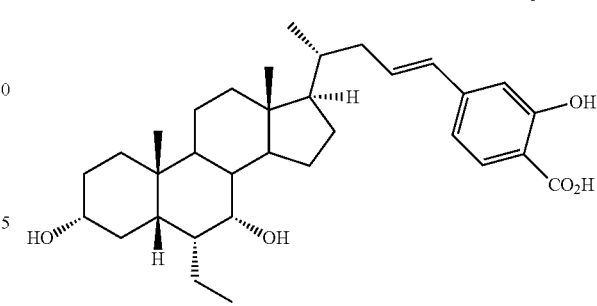
Compound 24
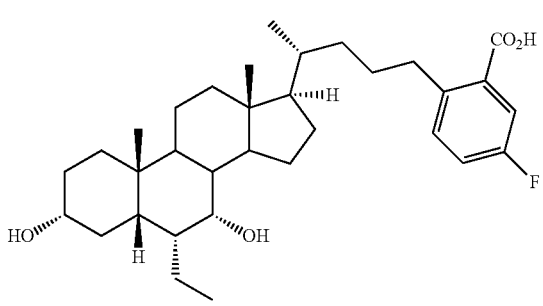
Compound 25
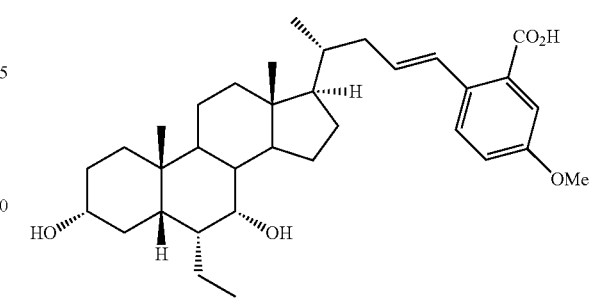
Compound 26
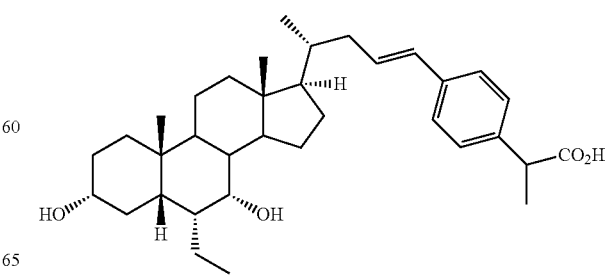

Compound 27
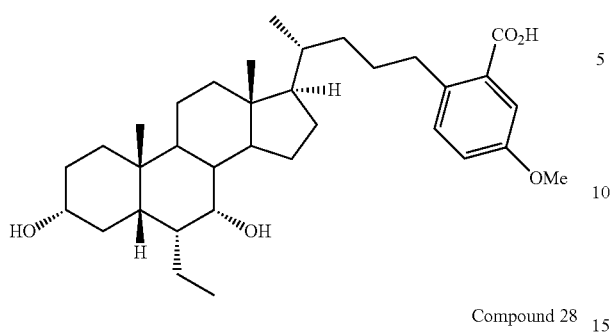
Compound 32
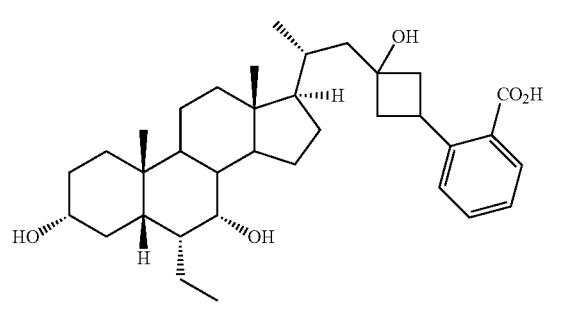
Compound 28
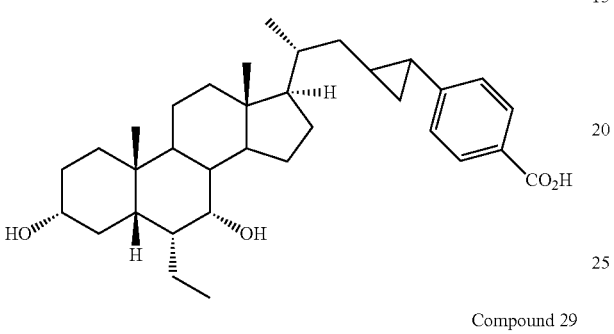
Compound 33
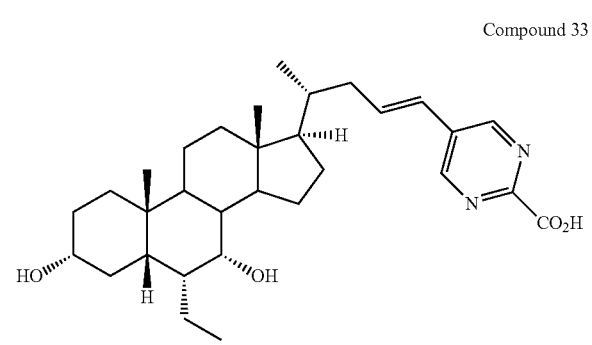
Compound 29
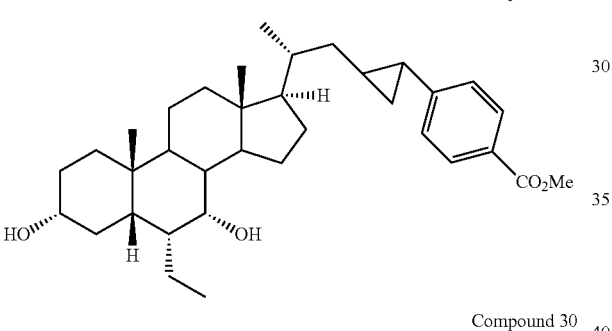
Compound 34
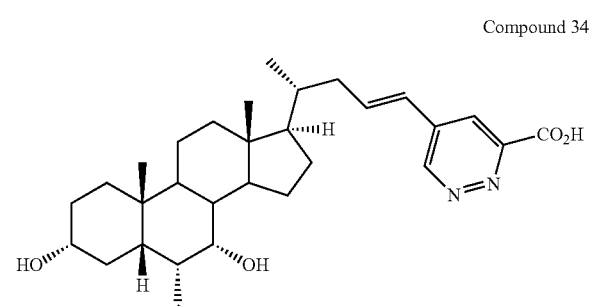
Compound 30
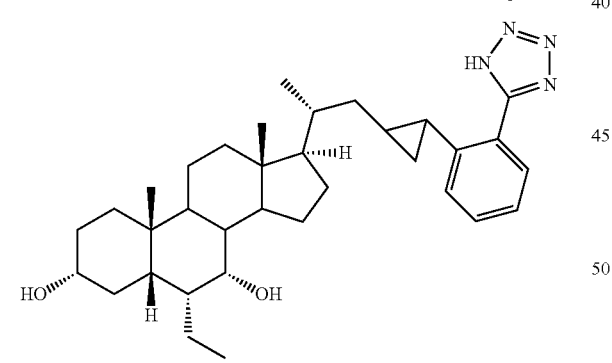
Compound 35
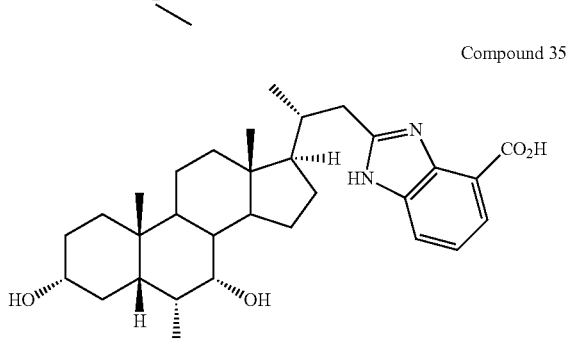
Compound 31
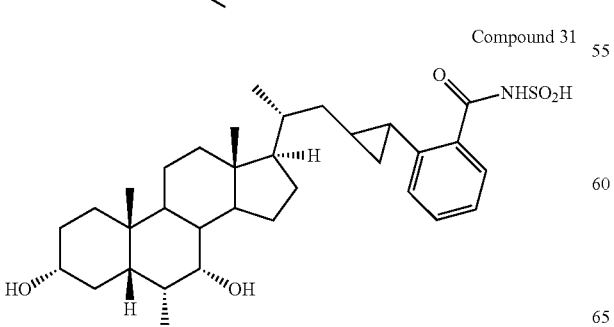
Compound 36
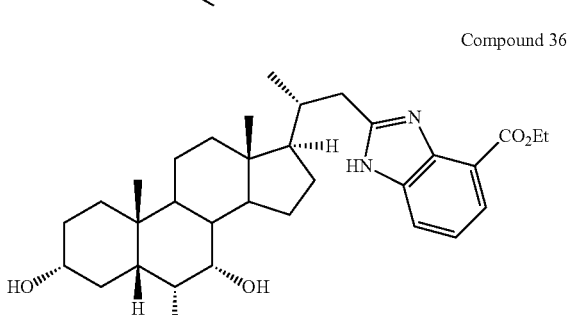

Compound 37

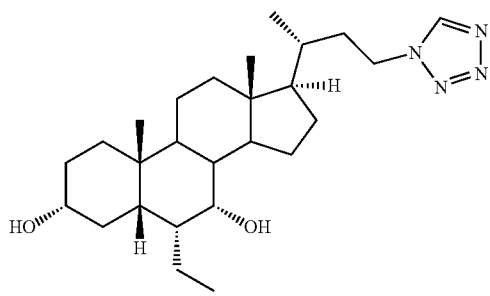

Compound 38

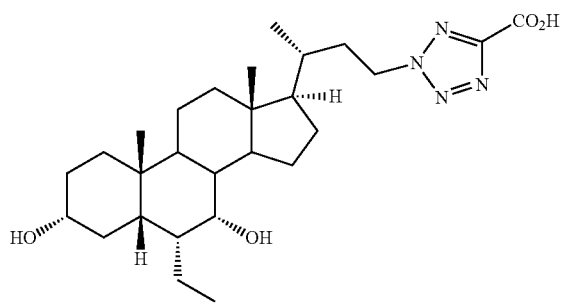

Compound 39

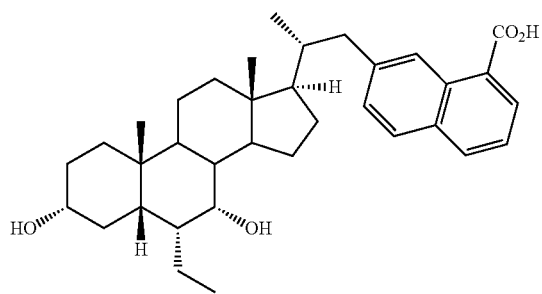

Compound 40

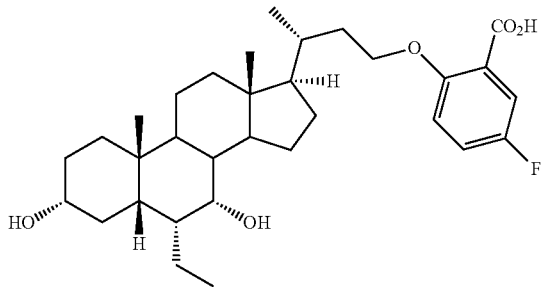

Compound 41

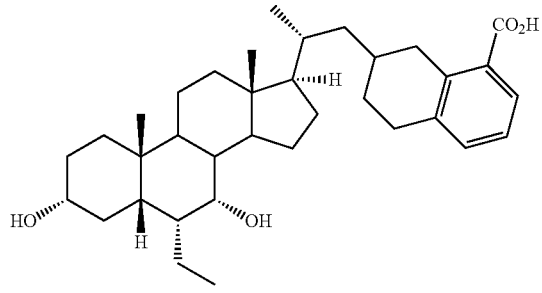

Compound 42

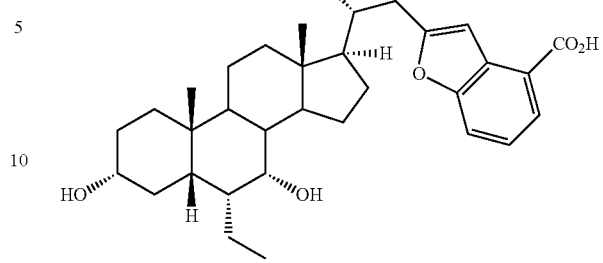

In certain embodiments, the present invention provides a method for the prevention or treatment of an FXR mediated disease or condition. The method comprises administering a therapeutically effective amount of a compound of formula (I). The present invention also provides the use of a compound of formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesteremia, or hyperlipidemia chronic liver disease, gastrointestinal disease, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In yet another embodiment, the invention provides the use of the compound or pharmaceutical composition of the invention, in the manufacture of a medicament for a treating or preventing a disease in a subject that involves modulation of the TGR5 receptor. The invention includes a method of treating or preventing a disease that involves modulation of the TGR5 receptor in a subject by administering a compound or pharmaceutical composition of the invention.

In certain embodiments, a disease that involves modulation of the TGR5 receptor is selected from metabolic disease, inflammatory disease, liver disease, autoimmune disease, cardiac disease, kidney disease, cancer, and gastrointestinal disease.

In one aspect, the invention provides for the use, wherein the disease is an inflammatory disease selected from allergy, osteoarthritis, appendicitis, bronchial asthma, pancreatitis, allergic rash, and psoriasis. The invention includes a method of treating or preventing an inflammatory disease selected from allergy, osteoarthritis, appendicitis, bronchial asthma, pancreatitis, allergic rash, and psoriasis.

In one aspect, the invention provides for the use, wherein the disease is an autoimmune disease selected from rheumatoid arthritis, multiple sclerosis, and type I diabetes. The invention includes a method of treating or preventing an autoimmune disease selected from rheumatoid arthritis, multiple sclerosis, and type I diabetes.

In one aspect, the invention provides for the use, wherein the disease is a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth. The invention includes a method of treating or preventing a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention provides for the use, wherein the disease is kidney disease selected from diabetic nephropathy, chronic renal failure, hypertensive nephrosclerosis, chronic glomerulonephritis, chronic transplant glomerulopathy, chronic interstitial nephritis, and polysystic kidney disease. The invention includes a method of treating or preventing kidney disease selected from diabetic nephropathy, chronic renal failure, hypertensive nephrosclerosis, chronic glomerulonephritis, chronic transplant glomerulopathy, chronic interstitial nephritis, and polysystic kidney disease.

In one aspect, the invention provides for the use, wherein the disease is cancer selected from colorectal cancer, liver cancer, heptacellular carcinoma, cholangio carcinoma, renal cancer, gastric cancer, pancreatic cancer, prostate cancer, and insulanoma. The invention includes a method of treating or preventing cancer selected from colorectal cancer, liver cancer, heptacellular carcinoma, cholangio carcinoma, renal cancer, gastric cancer, pancreatic cancer, prostate cancer, and insulanoma.

In one aspect, the compound is a selective FXR agonist over TGR5 activator.

In one aspect, the compound is a selective TGR5 agonist over FXR activator.

In one aspect, the compound is a dual agonist for both FXR and TGR5.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group Preferred alkyl groups include $C_1$-$C_8$ alkyl groups. Examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_8$ alkynyl groups. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as L in Formula I), the carbocycle group can be attached to the two other elements through any two substitutable ring atoms. A $C_4$-$C_6$ carbocycle has 4-6 ring atoms.

The term "cycloalkyl", as used herein, denotes a monovalent group derived from a monocyclic or polycyclic saturated carbocyclic ring compound by the removal of a single hydrogen atom. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl" as used herein, denotes a monovalent group derived from a monocyclic or polycyclic carbocyclic ring compound having at least one carbon-carbon double bond by the removal of a single hydrogen atom. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "alkoxyl," as used herein, refers to an alkyl or substituted alkyl group as defined above bounded through an oxygen atom (—O—), for example, —OR, wherein R is an alkyl or substituted alkyl.

The term "aminoalkyl" as used herein, refers to one or two alkyl or substituted alkyl groups as defined above bounded through a nitrogen atom, for example, —NRR', wherein one of R and R' is hydrogen and the other is alkyl or both R and R' are alkyl.

The terms "heterocyclic" or "heterocycloalkyl" can be used interchangeably and referred to a non-aromatic ring or a bi- or tri-cyclic group spiro, fused or bridged system, where (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, and tetrahydrofuryl. Such heterocyclic groups may be further substituted. Heteroaryl or heterocyclic groups can be C-attached or N-attached (where possible).

When the suffix "ene" is used in conjunction with other groups, this is intended to mean that the groups as defined herein have two single bonds as points of attachment to other groups, for example, the term "alkylene" as employed herein refers to an "alkyl" group as defined above which is linked to two other groups. Other examples include the term "alkenylene," "alkynylene," "alkoxylene," "aminoalkylene," "cycloalkylene," and "heterocycloalkylene," wherein "alkenyl," "alkynyl," "alkoxyl," "aminoalkyl," "cycloalkyl," and "heterocycloalkyl," are defined as above.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_{12}$-alkyl, $C_2$-$C_{12}$-alkenyl, $C_2$-$C_{12}$-alkynyl, $C_3$-$C_{12}$-cycloalkyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O—heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH— aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)— heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$— aryl, —NHCO$_2$— heteroaryl, —NHCO$_2$— heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkynyl, —SO$_2$NH—$C_3$-$C_{12}$-cycloalkyl, —SO$_2$NH— aryl, —SO$_2$NH-heteroaryl, —SO$_2$NH— heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl, are intended to be monovalent or divalent. Thus, alkylene, alkenylene, and alkynylene, cycloalkylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2, 2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The terms "halo" and "halogen," as used herein, refer to an atom selected from fluorine, chlorine, bromine and iodine.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs,* Elsevier (1985); Widder, et al. (ed.), *Methods in Enzymology,* Vol. 4, Academic Press (1985); Krogsgaard-Larsen, et al., (ed). "Design and Application of Prodrugs, *Textbook of Drug Design and Development,* Chapter 5, 113-191 (1991); Bundgaard, et al., *Journal of Drug Deliver Reviews,* 8:1-38(1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional nontoxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DBU for 1, 8-Diazabicycloundec-7-ene;
DCC for N, N'-dicyclohexylcarbodiimide;

DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
DUPHOS for

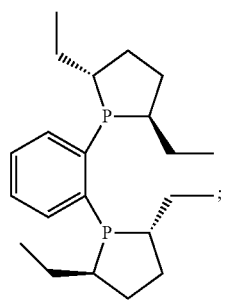 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for room temperature;
RT-PCR for reverse transcription-polymerase chain reaction;
TBME for tert-butyl methyl ether;
TEA for triethyl amine;
Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TBS for t-Butyldimethylsilyl;
TMS for trimethylsilyl;
T3P for propyl phosphoric anhydride;
TPAP tetrapropylammonium perruthenate;
TPP or PPh$_3$ for triphenylphosphine;
TrCl for trityl chloride;
DMTrCl for 4,4'-dimethoxytrityl chloride;
tBOC or Boc for tert-butyloxy carbonyl;

Xantphos for 4,5-Bis-diphenylphosphanyl-9,9-dimethyl-9H-xanthene; and
Zhan-1B for:

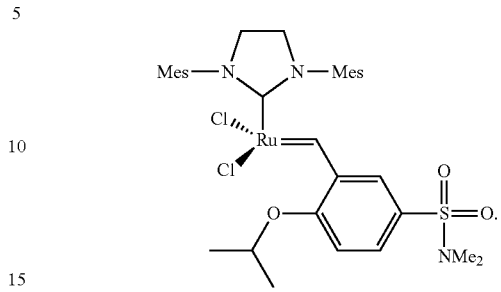

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel bile acid analogs of the compound of formula (1-3) are prepared from the bile acid compound of formula (1-1) and the compound of formula (1-2), where X is halide or triflate, preferably I, Br, Cl or OTf, and Ar and R$_1$ are defined as previously. Thus, the compound of formula (1-3) is formed by the Heck reaction of the alkene of formula (1-1) with the halide or triflate of formula (1-2) in the presence of a base and a palladium catalyst with or without a ligand. The catalyst can be selected from, but not limited to, Pd(PPh$_3$)$_4$, PdCl$_2$, Pd(OAc)$_2$. The ligand can be, but is not limited to, PPh$_3$, PHOX or BINAP. The base can be, but is not limited to, Et$_3$N, K$_2$CO$_3$ or NaOAc. The Heck reaction can be carried out in neat conditions or in a solvent such as, but not limited to, DMF, DMSO, MeOH, THF or toluene at a temperature from 20° C. to 180° C. (Vadola P. A., et al., *J. Org. Cheml.* 2012, 77, 6689-6702).

Scheme 1

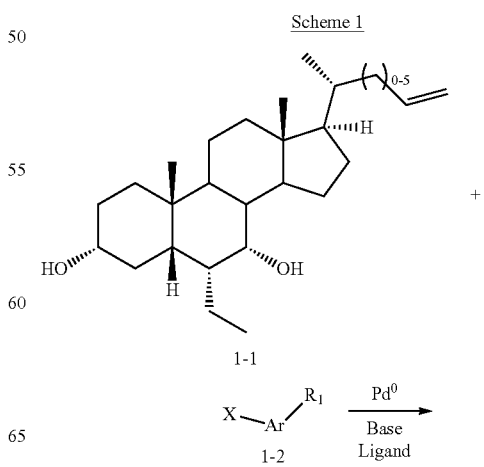

-continued

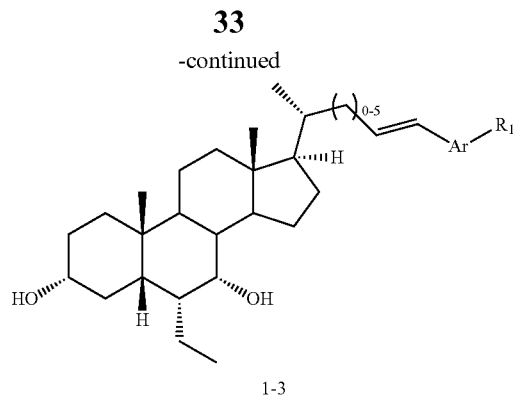

1-3

Alternatively, the compound of formula (1-3) can be prepared by the Cross Metathesis reaction (Donohoe, T. J., et al., *Org. Biomol. Chem.* 2012, 10, 1322-1328) of alkene of formula (1-1) with the (hetero)aryl alkene of formula (2-1) in the presence of a catalyst such as, but not limited to, Grubbs catalyst, Schrock catalyst or Zhan catalyst, wherein Ar and $R_1$ are defined as previously (Scheme 2).

Scheme 2

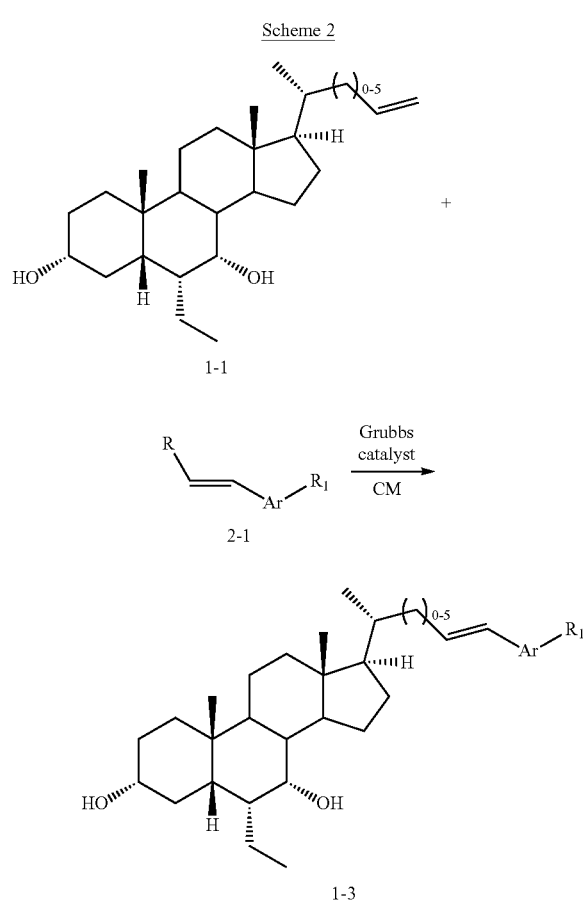

R = H, alkyl, alkoxyl or aryl

The alkane of formula (3-1) is then prepared from the alkene of formula (1-3) by hydrogenation using catalyst such as, but not limited to, Pd/C, Pd(OAc)$_2$, PtO$_2$ or Ru(Ph$_3$)$_2$Cl$_2$, or by reduction with, but not limited to, NaBH$_4$ or Na (Scheme 3).

Scheme 3

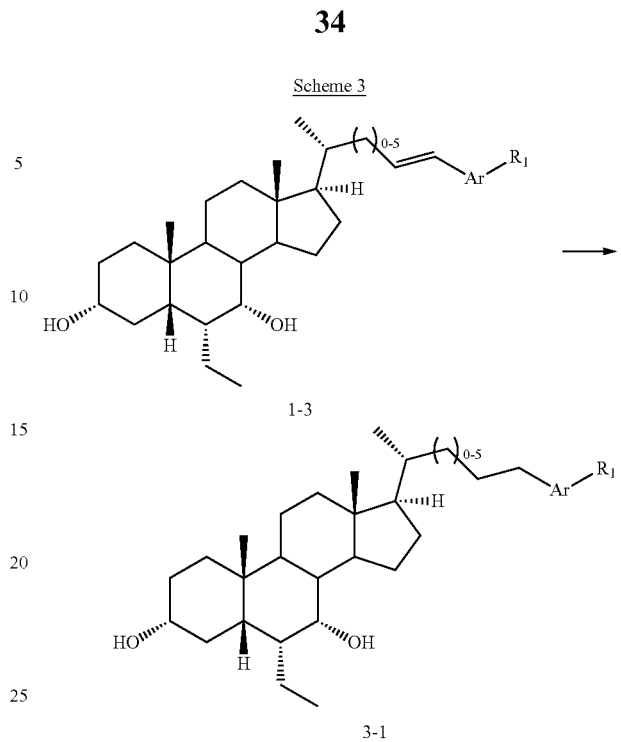

The starting material alkene of formula (1-1) is prepared either by Grieco elimination from the alcohol of formula (4-1) (Scheme 4) or by halogen elimination from the halogen compound of formula (5-2) (Scheme 5), wherein $R_4$ and $R_5$ are as previously defined. Deprotection reagent is, but not limited to, HCl, HBr, TFA, TBAF or sulfuric acid. Halogen elimination can be achieved using a base, such as, but not limited to, NaOH, KOH, t-BuOK, t-BuONa, NaOMe or NaH, in a solvent, such as THF, MeOH or DMF, at a temperature from 0° C. to 160° C.

Scheme 4

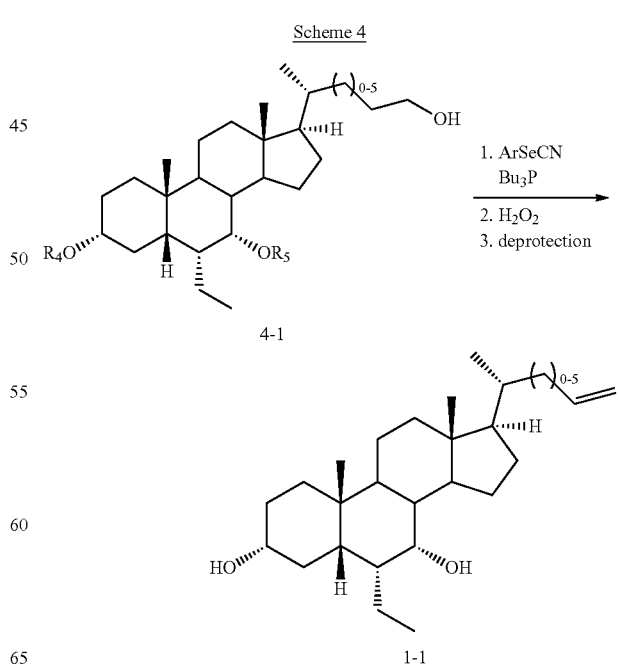

Scheme 5

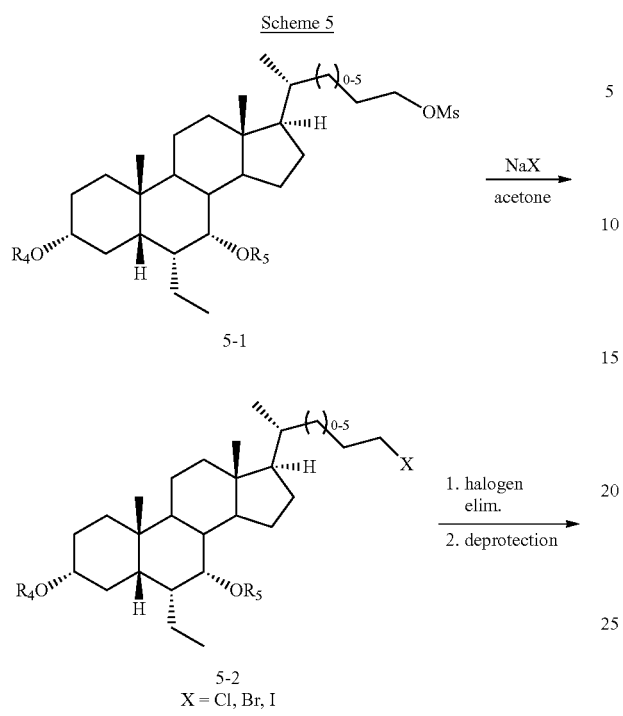

5-2
X = Cl, Br, I

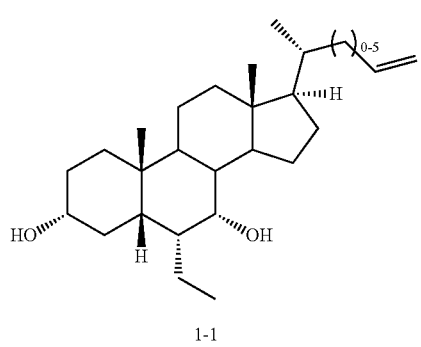

1-1

Scheme 6 illustrates the preparation of tetrazole compound of formula (6-2) and formula (6-3), wherein $R_4$ and $R_5$ are as previously defined. The base is, but not limited to, $K_2CO_3$, $Na_2CO_3$, KOH, NaOH, t-BuOK or NaH. The deprotection reagent can be, but is not limited to, HCl, HBr, TFA, TBAF or sulfuric acid.

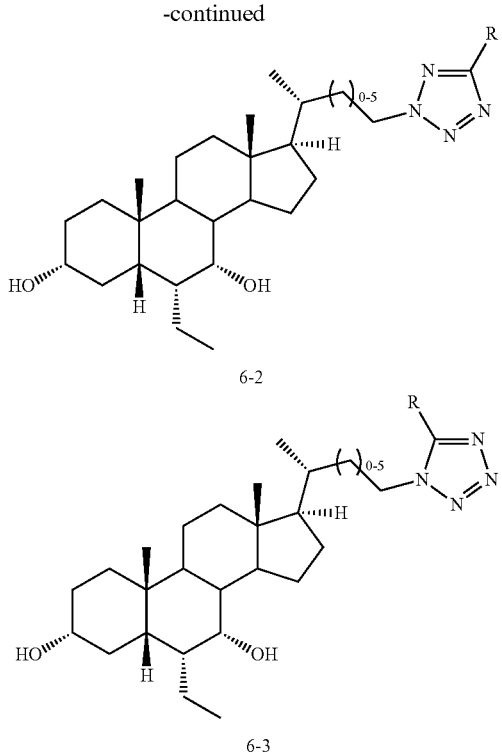

6-3
R = H, $CO_2H$, $CH_2CO_2H$

Scheme 7 illustrates the preparation of the benzoxazole compound of formula (7-4) from the acid compound of formula (7-1) and the aniline compound of formula (7-2), wherein the $R_1$, $R_4$, and $R_5$ are defined as previously. Thus, the compound of formula (7-1) is first coupled with the aniline compound of formula (7-2) under suitable coupling condition to afford the compound of formula (7-3). The coupling reagent can be selected from, but not limited to, DCC, EDC, CDI, di-isopropyl carbodiimide, BOP-Cl, PyBOP, PyAOP, T3P, TFFH or HATU. Suitable bases include, but are not limited to, triethylamine, diisopropylethylamine, DBU, N-methylmorpholine or DMAP. The coupling reaction is carried out in an aprotic solvent such as, but not limited to, $CH_2Cl_2$, DMF or THF at a temperature from 0° C. to about 150° C. The benzoxazole compound of formula (7-4) is then formed from the compound of formula (7-3) under suitable dehydration condition followed by deprotection. Dehydration reagent can be, but not limited to, p-TsOH, MsOH or T3P, and solvent can be selected from, but not limited to, toluene, DMF or THF. Deprotection reagent is, but not limited to, HCl, HBr, TFA, TBAF or sulfuric acid.

Scheme 6

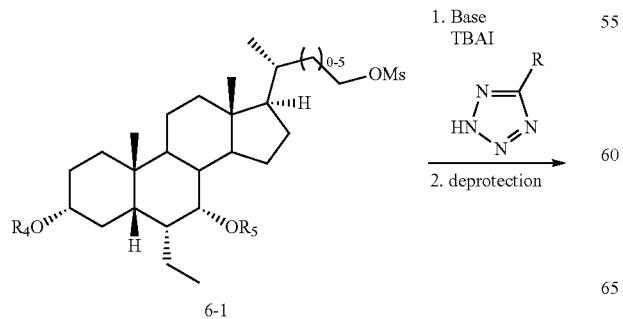

Scheme 7

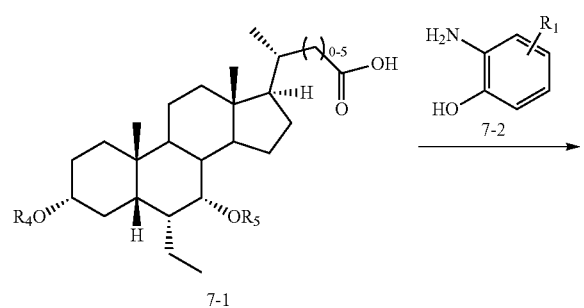

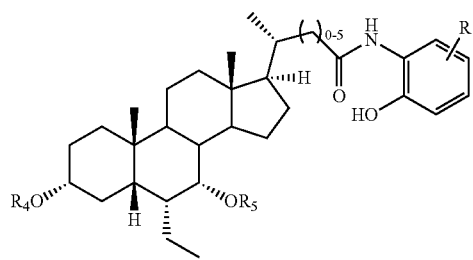

7-3

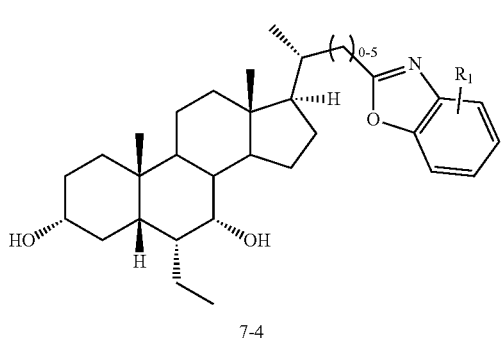

7-4

Scheme 8 illustrates the synthesis of the aryl ether compound of formula (8-3) from the alcohol of formula (8-1) and the phenol of formula (8-2) by Mitsunobu reaction followed by deprotection (Manhas, M. S., at al., *J. Chem. Soc., Perkin Trans.*, 1975, 461-463), wherein the $R_1$, $R_4$, and $R_5$ are defined as previously. The deprotection reagent can be, but is not limited to, HCl, HBr, TFA, TBAF or sulfuric acid.

Scheme 8

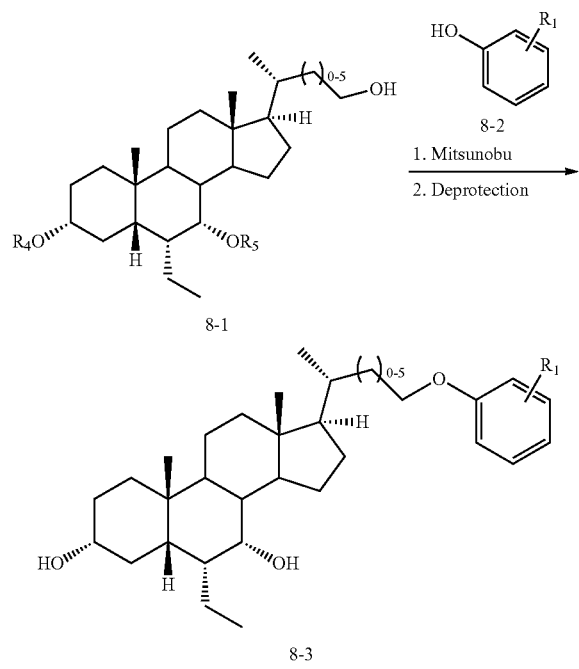

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Synthesis of Intermediates

Scheme 9

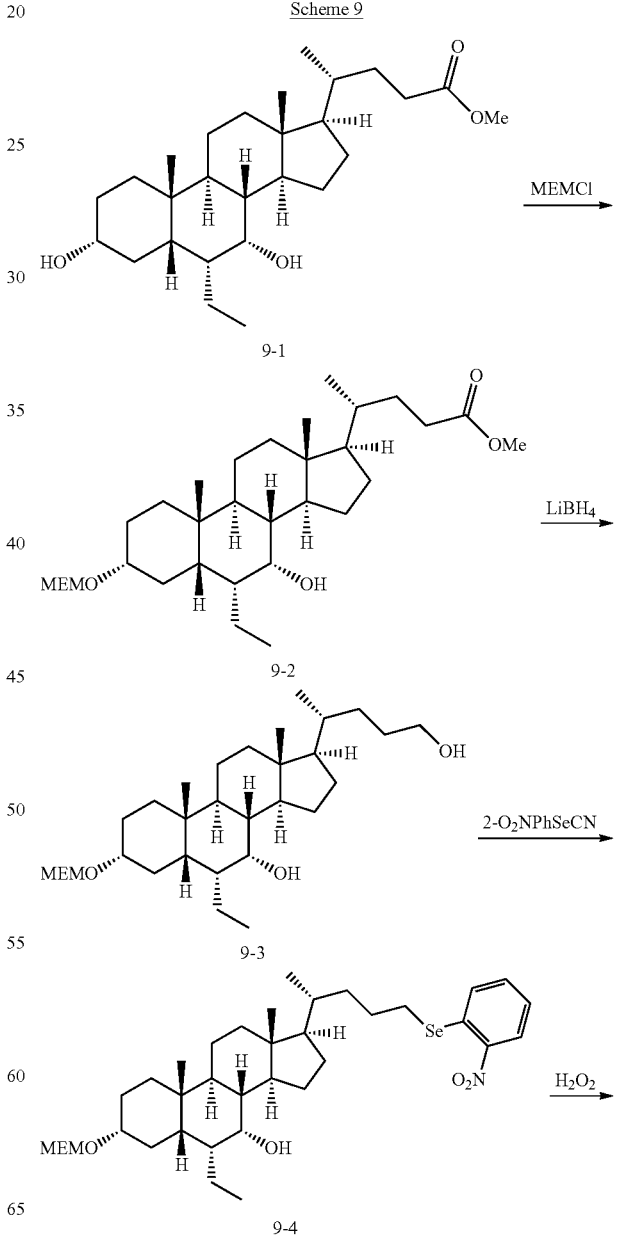

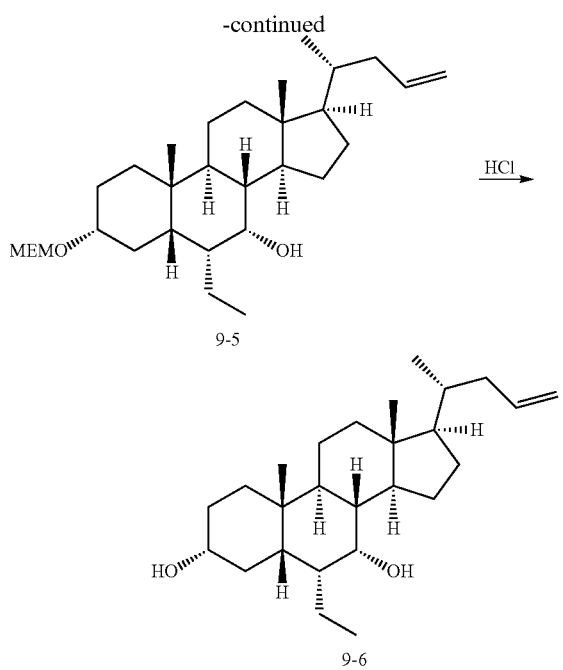

up to RT and stirred for 20 h, quenched with H₂O/brine (1/1), and extracted with EtOAc. The combined organic layers were washed with brine and concentrated. DCM was added to the residue, and the solid was removed by filtration and washed with DCM. The filtrate was concentrated. The residue was purified by chromatography on silica gel using hexane/EtOAc (100/0 to 70/30, 10 min) to obtain a product (9-5) as a pale yellow oil (701 mg, 87% yield).

Step 5:

A solution of (9-5) (28 mg, 0.06 mmol) in THF (2 mL) at RT was treated with HCl (37%, 0.1 mL). The reaction mixture was stirred at RT for 2 h, quenched with sat NaHCO₃, and extracted with EtOAc. The combined organic layers were washed with brine and concentrated. The residue was purified by chromatography on silica gel using hexane/EtOAc (100/0 to 60/40, 10 min) to afford a product as a white foam (9-6) (20 mg, 87% yield). LC-MS observed 2M+1=777.68 (Calcd. 777.66). $^1$HNMR (500 MHz, CDCl₃): δ 5.77 (1H, m), 4.90 (2H, d, J=11.5 Hz), 3.71 (1H, s), 3.40 (1H, br s), 0.90 (6H, br s), 0.67 (3H, s).

Step 1 (Scheme 9):

MEMCl (2.3 mL, 20 mmol) was added to a stirred solution of (9-1) (4.35 g, 10 mmol) (J. Med. Chem. 2014, 57, 937-954) and DIPEA (10.3 mL, 30 mmol) in DCM (100 mL) at 0° C. under N₂. The resulting reaction mixture was allowed to warm up to RT and stirred overnight, then quenched with water (50 mL) and 1 N HCl (50 mL). The organic layer was dried over anhydrous sodium sulfate, filtered, and concentrated to give 6.5 g of crude product (9-2), which was used directly for next step. LC-MS observed 2M+NH₄=1062.83 (Calcd. 1062.81).

Step 2:

The above mentioned crude product (9-2) (4.18 g, 8.0 mmol) was first dissolved in THF (30 mL) at 0° C. under N₂, dry MeOH (1.28 mL, 32 mmol) was added, followed by slow addition of LiBH₄ (697 mg, 32 mmol). The mixture was stirred at 0° C. for 6 h, TLC and LC-MS analysis showed partial conversion of the starting material, more LiBH₄ (348 mg, 16 mmol) was then added. The mixture was allowed to warm up to RT and stirred overnight, quenched with 1 M aq. NaOH (20 mL), and extracted with ethyl acetate. The combined organic layers were washed with brine and concentrated. The residue was purified by chromatography on silica gel using hexane/acetone (100/0 to 60/40, 10 min) to afford alcohol product (9-3) (3.2 g, 94% yield based on 86% conversion) as a white foam. LC-MS observed 2M+NH₄=1006.83 (Calcd. 1006.83).

Step 3:

To a stirred solution of (9-3) (870 mg, 1.76 mmol) in THF (10 mL) at RT under N₂ was added 2-nitrophenyl selenocyanate (800 mg, 3.52 mmol), followed by PBu₃ (0.87 mL, 3.52 mmol). The reaction mixture was stirred at RT for 3 h, and then concentrated. The residue was purified by chromatography on silica gel using hexane/EtOAc (100/0 to 60/40, 10 min) to give a product (9-4) as a yellow oil (1.14 g, 95% yield).

Step 4:

To a stirred solution of (9-4) (1.14 g, 1.68 mmol) in THF (20 mL) at RT was added slowly H₂O₂ (30% in H₂O, 3.8 mL, 33.6 mmol). The reaction mixture was allowed to warm

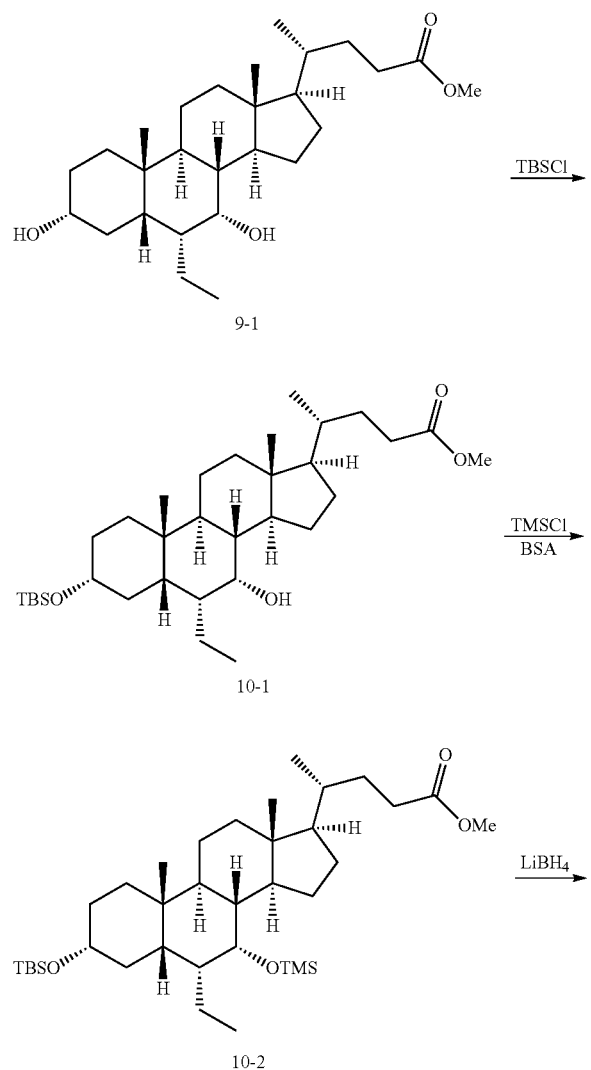

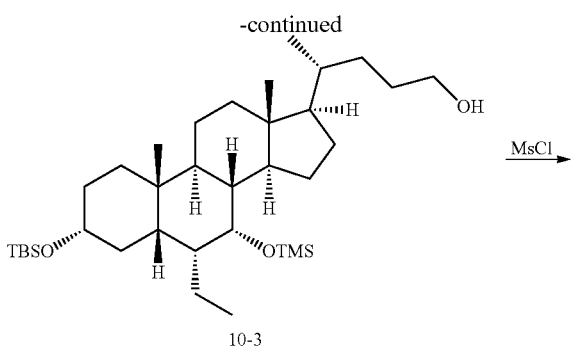

10-3

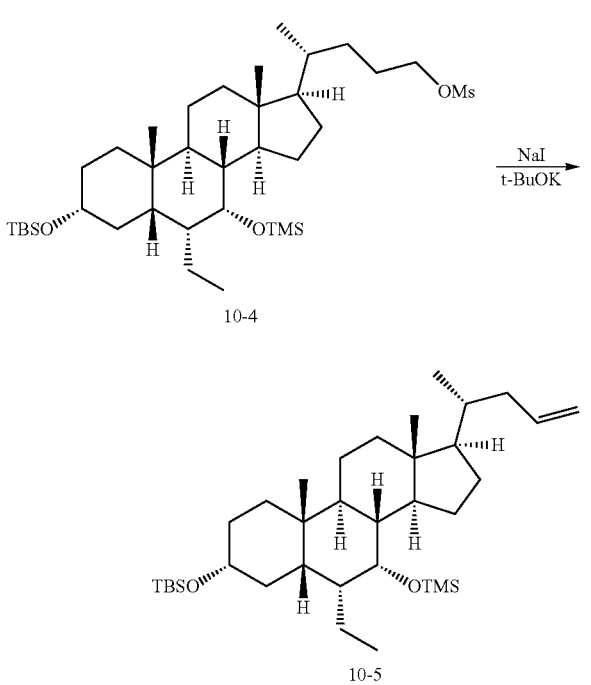

10-4

10-5

Step 1 (Scheme 10):

TBSCl (19.5 g, 129 mmol) was added to a stirred solution of (9-1) (50.9 g, 117 mmol) and imidazole (24.0 g, 351 mmol) in THF/DMF (400 mL/100 mL) at 0° C. under $N_2$. The resulting reaction mixture was allowed to warm up to RT and stirred overnight, then quenched with MeOH, 2 N HCl and 7% citric acid, and extracted with toluene. The organic layer was washed with $H_2O$, dried over anhydrous sodium sulfate, filtered, and concentrated to give a crude product (10-1), which was used directly for next step.

Step 2:

To a stirred solution of (10-1) and NMI (18.75 mL, 234 mmol) in DCM at 0° C. under $N_2$ was added BSA (72 mL, 292 mmol), followed by TMSCl (22.4 mL, 175.5 mmol). The reaction mixture was allowed to warm up to RT and stirred for 1 h, quenched slowly with MeOH at 0° C. and 5% citric acid, and extracted with EtOAc. The organic layer was washed with brine, dried over anhydrous sodium sulfate, filtered, and concentrated to give a crude product (10-2), which was used directly for next step.

Step 3:

The above crude product (10-2) (117 mmol) was first dissolved in THF (100 mL) at 0° C. under $N_2$, dry MeOH (18.3 ml) was added, followed by slow addition of 2M $LiBH_4$ in THF (300 mL). The mixture was allowed to warm up to RT and stirred for 2 h, quenched with 1 M aq. NaOH, and extracted with ethyl acetate. The combined organic layers were washed with brine, dried over $Na_2SO_4$, and concentrated. The residue was purified by chromatography on silica gel using hexane/acetone (100/0 to 75/25, 15 min) to afford alcohol product (10-3) (64.5 g, 92 yield % overall).

Step 4:

To a stirred solution of (10-3) (28 g, 47 mmol) and $Et_3N$ (10 mL, 71 mmol) in DCM at 0° C. under $N_2$ was added slowly MsCl (4 mL, 52 mmol) over 30 min. The reaction mixture was stirred at 0° C. for another 30 min and then quenched with $H_2O$. The organic layer was washed with 4% $NaHCO_3$, dried over anhydrous sodium sulfate, filtered, and concentrated to give a product (10-4) as a white foam (31 g, 99% yield).

Step 5:

NaI (2.25 g, 15 mmol) was added to a solution of (10-4) (3.36 g, 5 mmol) in acetone (50 mL). The mixture was heated to 60° C. and stirred overnight, cooled down to RT, concentrated to remove acetone, then diluted with $H_2O$/brine (1/1), and extracted with EtOAc. The combined organic layers were washed with brine and concentrated to give a white foam (3.5 g, 99% yield), which (2.81 g, 4 mmol) was dissolved in THF (25 mL) and treated with t-BuOK (1.35 g, 12 mmol). The mixture was stirred overnight at RT, quenched with 5% $NaHCO_3$ and brine, and extracted with EtOAc. The combined organic layers were washed with brine and concentrated. The residue was purified by chromatography on silica gel using hexane/EtOAc (100/0 to 85/15, 10 min) to afford a product as a white foam (10-5) (1.4 g, 61% yield).

Scheme 11

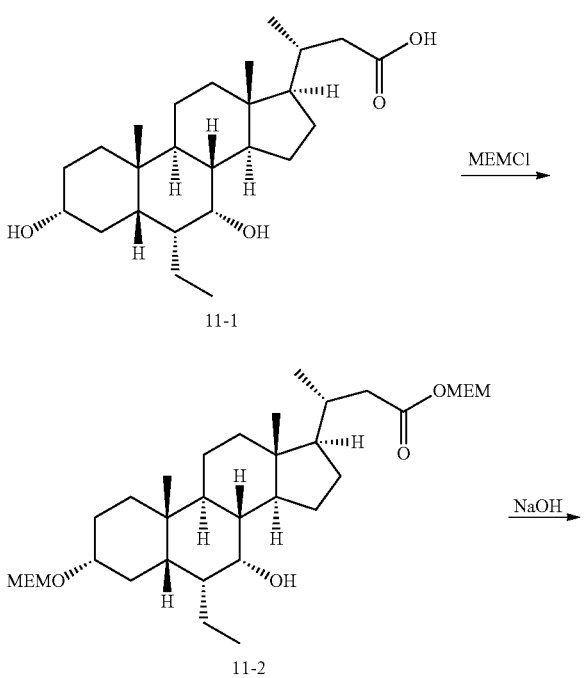

11-1

11-2

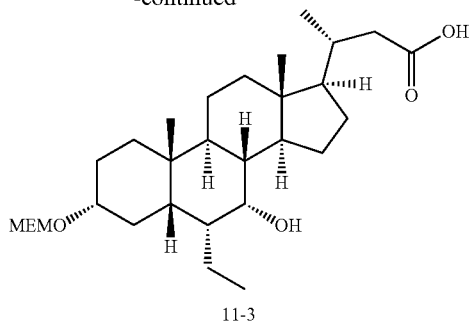

Step 1 (Scheme 11):

The bile acid analog (11-1) (2.033 g, 5.0 mmol) (J. Med. Chem. 2014, 57, 937-954) was first dissolved in DCM at 0° C. (60 mL). DIPEA (6.97 mL, 40 mmol) was added to the solution, followed by MEMCl (2.3 mL, 20 mmol). The reaction mixture was allowed to warm up to RT and stirred overnight, quenched with 1N HCl/brine (1/1), and extracted with EtOAc. The combined organic layers were washed with brine and concentrated. The residue was purified by chromatography on silica gel using hexane/acetone (100/0 to 70/30, 10 min) to give a product (11-2) as a colorless oil (2.81 g, 96% yield). LC-MS observed M+NH$_4$=600.45 (Calcd. 600.41).

Step 2:

To a stirred solution of (11-2) (1.6 g, 2.75 mmol) in MeOH/H$_2$O (3/1, 8 mL) at RT was added 50% aq. NaOH (0.75 mL, 8.22 mmol). The reaction mixture was heated to 50° C. and stirred for 3 h, then quenched with 1N HCl/brine (1/1), and extracted with EtOAc. The combined organic layers were washed with brine and concentrated. The residue was purified by chromatography on silica gel using hexane/acetone (100/0 to 60/40, 10 min) to afford a product (11-3) as a pale yellow solid (1.1 g, 81% yield). LC-MS observed M−1=593.28 (Calcd. 593.36).

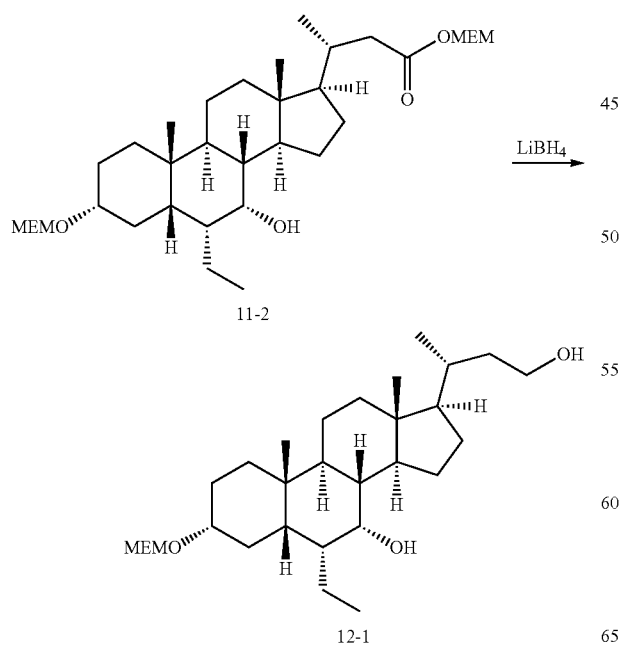

Scheme 12

As shown in Scheme 12, the MEM ester (11-2) (1.15 g, 2.0 mmol) was first dissolved in THF (4 mL) at 0° C. under N$_2$, dry MeOH (0.32 ml) was added, followed by slow addition of 2M LiBH$_4$ in THF (6 mL). The mixture was allowed to warm up to RT and stirred overnight, quenched with 1 M aq. NaOH and brine, and extracted with ethyl acetate. The combined organic layers were washed with brine, dried over Na$_2$SO$_4$, and concentrated. The residue was purified by chromatography on silica gel using hexane/acetone (100/0 to 60/40, 10 min) to the afford alcohol product as a white foam (12-1) (720 mg, 75% yield). LC-MS observed 2M+NH$_4$=978.77 (Calcd. 978.79).

Example 1

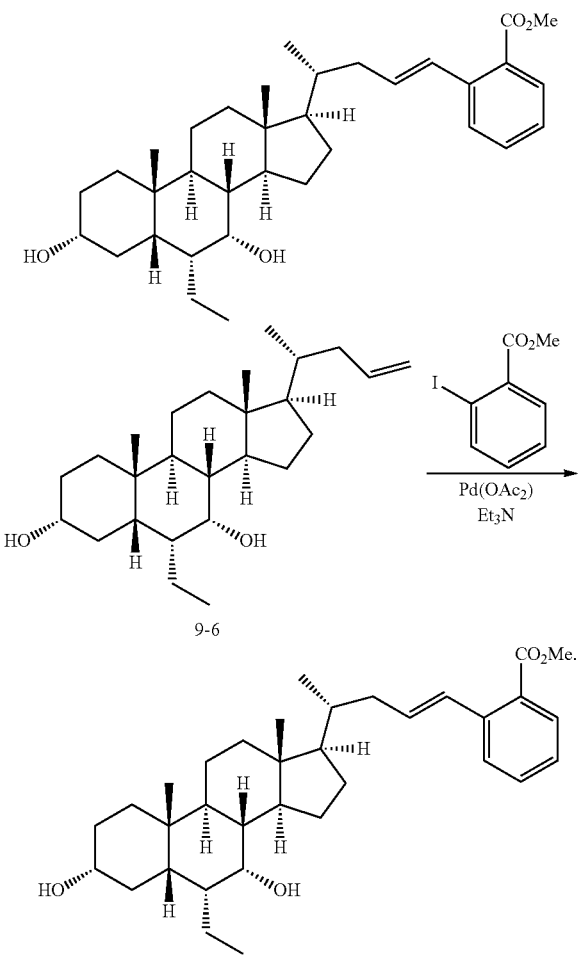

Example 1

A solution of (9-6) (58 mg, 0.15 mmol) and methyl 2-iodobenzoate (53 mg, 0.20 mmol) in DMF (1.5 mL) at RT was degassed with N$_2$ for 10 min, Et$_3$N and Pd(OAc)$_2$ were added, and degassed for another 10 min. The reaction mixture was heated to 80° C. and stirred overnight, cooled down to RT, quenched with 3% citric acid and brine, and extracted with EtOAc. The combined organic layers were washed with brine and concentrated. The residue was purified by chromatography on silica gel using hexane/EtOAc (100/0 to 60/40, 10 min) to obtain example 1 as a white solid (54 mg, 86% yield). LC-MS observed 2M+NH$_4$=1062.78 (Calcd. 1062.77).

Example 2

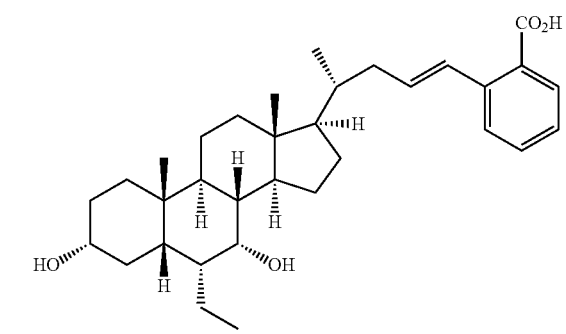

Example 2

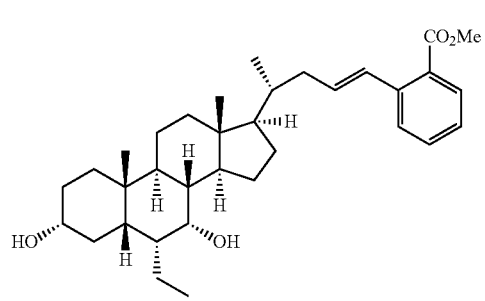

Example 1

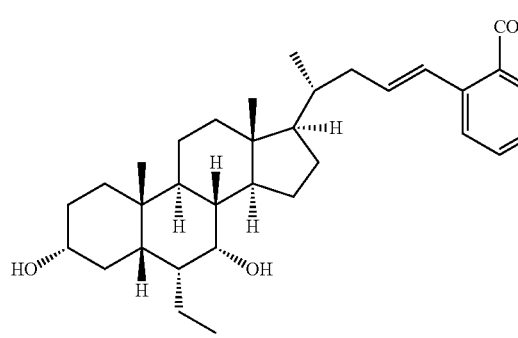

Example 2

To a solution of example 1 (40 mg, 0.08 mmol) in THF/MeOH/H$_2$O (3/1/1, 4 mL) at RT was added LiOH monohydrate (61 mg, 1.45 mmol). The reaction mixture was stirred overnight, then quenched with 1N HCl/brine (1/1), and extracted with EtOAc. The combined organic layers were washed with brine and concentrated. The residue was purified by chromatography on silica gel using DCM/MeOH (100/0 to 85/15, 10 min) to afford a product example 2 as a white solid (28 mg, 74% yield). LC-MS observed M−1=507.37 (Calcd. 507.36). $^1$HNMR (500 MHz, CDCl$_3$): δ 7.99 (1H, d, J=9.0 Hz), 7.54 (1H, d, J=9.0 Hz), 7.50 (1H, t, J=9.0 Hz), 7.28 (1H, t, J=9.0 Hz), 7.19 (1H, d, J=16.0 Hz), 6.10 (1H, m), 3.72 (1H, s), 3.41 (1H, br s), 0.90 (6H, br s), 0.69 (3H, s).

Example 3

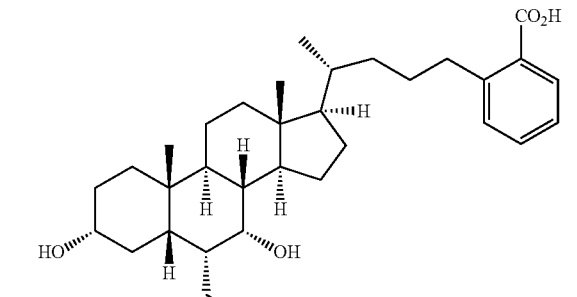

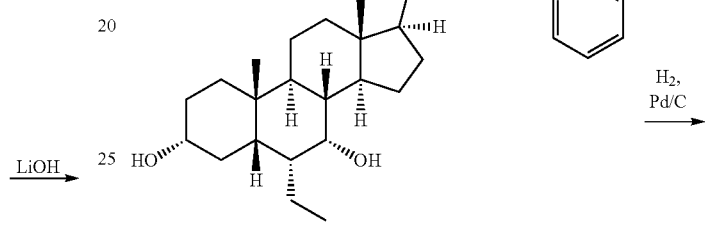

Example 2

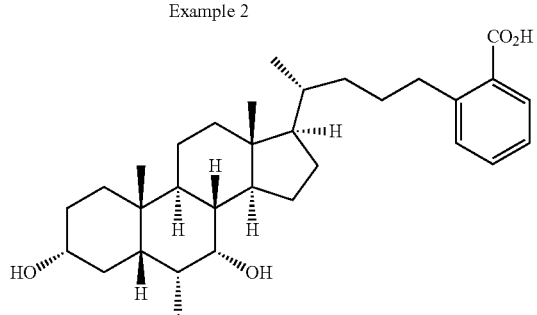

Example 3

Pd/C (10%, 6 mg) was first added to a solution of example 2 (15 mg, 0.03 mmol) in MeOH/EtOAc (1/1, 2 mL). The mixture was first degassed with N$_2$ for 15 min and then stirred under H$_2$ for 16 h, filtered through celite, and the solid was washed with MeOH and EtOAc. The filtrate was concentrated and dried to afford example 3 as a white solid (13 mg, 93% yield). LC-MS observed M−1=509.36 (Calcd. 509.36). $^1$HNMR (500 MHz, CDCl$_3$): δ 7.92 (2H, m), 7.43 (1H, m), 7.42 (1H, m), 3.71 (1H, s), 3.41 (1H, br s), 2.66 (1H, m), 2.61 (1H, m), 0.89 (6H, br s), 0.66 (3H, s).

Example 4

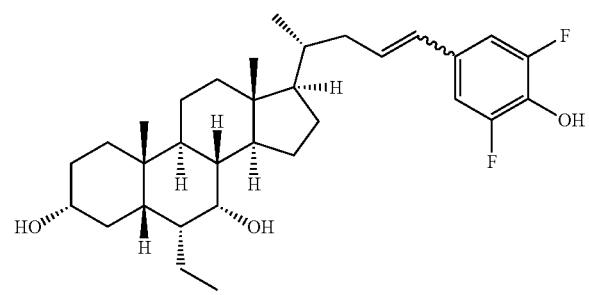

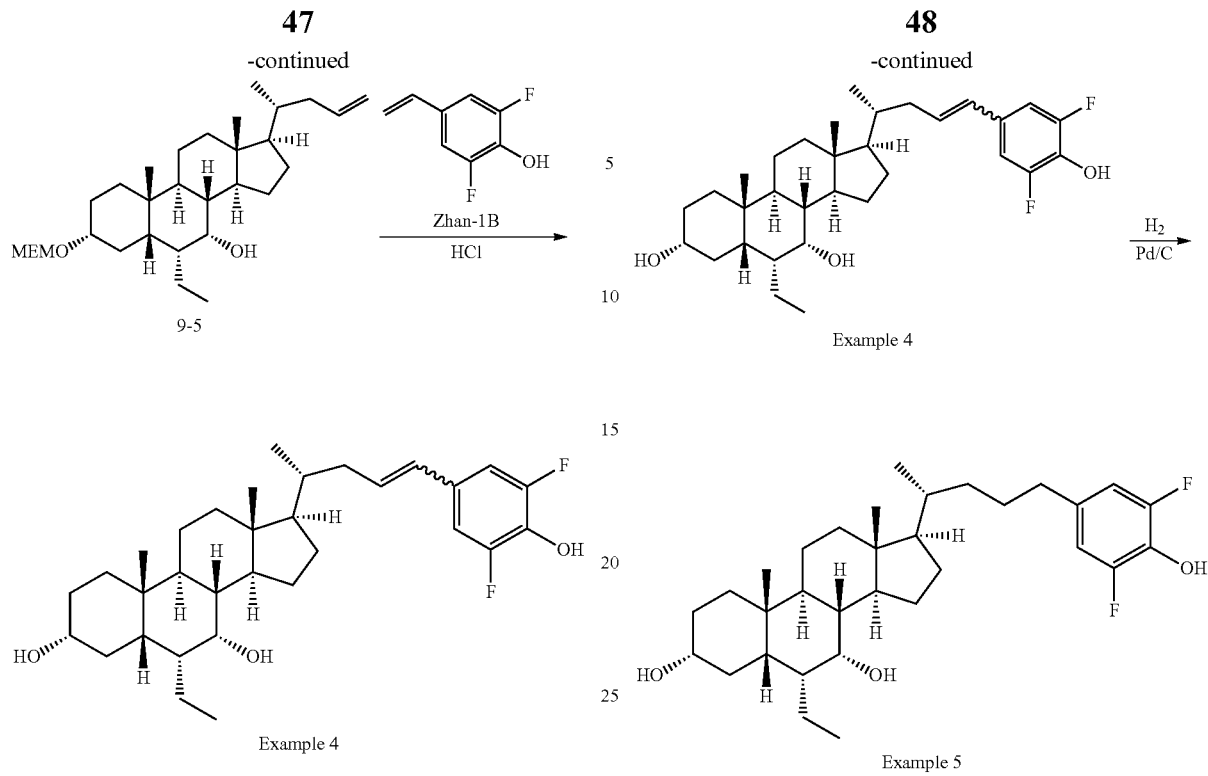

Example 4

A mixture of (9-5) (95 mg, 0.2 mmol) and 2,4-difluoro-4-vinylphenol (312 mg, 2.0 mmol) in toluene (5 mL) was degassed with $N_2$ at 60° C. for 15 min. Zhan-1B catalyst (29 mg, 0.04 mmol) was then added. The mixture was stirred at 60° C. for 4 h, 2-mercapto nicotinic acid (31 mg, 0.2 mmol) and DIPEA (35 µL, 0.2 mmol) were then added and stirred for another 30 min before cooled down to RT. Diluted with EtOAc and brine, and the organic layer was washed with brine and concentrated. The residue was purified by chromatography on silica gel using hexane/EtOAc (100/0 to 65/35, 10 min) to give the CM product as a pale yellow oil (20 mg, 17% yield), which was dissolved in THF (2 mL) and treated with HCl (37%, 0.05 mL). The mixture was stirred at RT for 1.5 h, quenched with brine, and extracted with EtOAc. The combined organic layers were washed with brine and concentrated. The residue was purified by chromatography on silica gel using hexane/EtOAc (100/0 to 50/50, 10 min) to obtain example 4 as a white solid (8 mg, 47% yield). LC-MS observed M+HCO$_2$H−1=561.34 (Calcd. 561.35).

Example 5

Pd/C (10%, 10 mg) was first added to a solution of example 4 (38 mg, 0.07 mmol) in MeOH/EtOAc (1/1, 2 mL). The mixture was first degassed with $N_2$ for 15 min and then stirred under $H_2$ for 16 h, filtered through celite, and the solid was washed with MeOH and EtOAc. The filtrate was concentrated and dried to provide a product as a white solid (35 mg, 92% yield). LC-MS observed M−1=517.35 (Calcd. 517.36).

Example 6

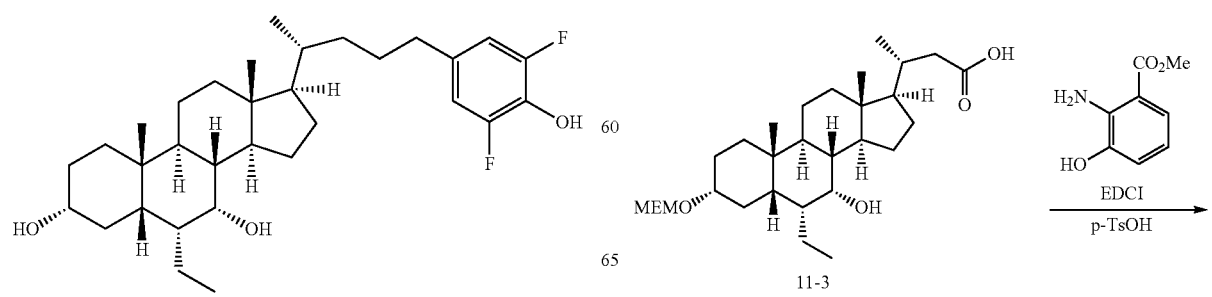

-continued

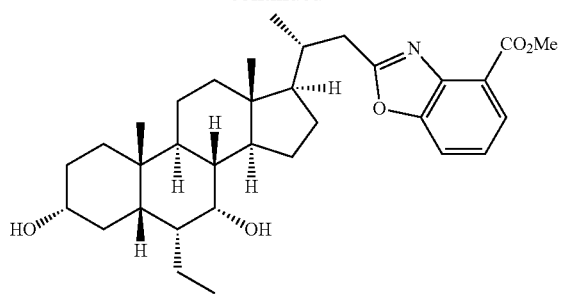

Example 6

-continued

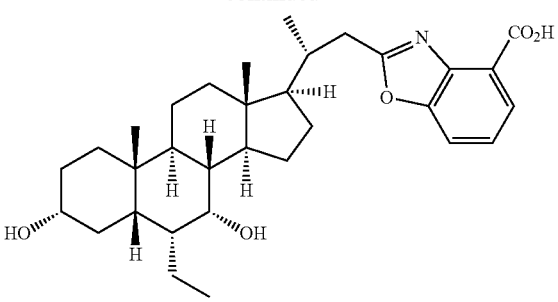

Example 7

To a solution of (11-3) (148 mg, 0.3 mmol), EDCI (115 mg, 0.6 mmol), and DMAP (73 mg, 0.6 mmol) in DCM/DMF (4/1, 5 mL) at RT was added methyl 2-amino-3-hydroxylbenzoate (100 mg, 0.6 mmol). The reaction mixture was stirred at RT for 3 h, then quenched with 3% citric acid/brine (1/1), and extracted with EtOAc. The combined organic layers were washed with brine and concentrated. The residue was purified by chromatography on silica gel using hexane/EtOAc (100/0 to 60/40, 10 min) to offer a product as a brown oil (170 mg, 88% yield), which was dissolved in toluene (5 mL) and treated with p-TsOH (10 mg, 0.05 mmol). The mixture was heated to 110° C. and stirred for 50 min, cooled down to RT, quenched with sat NaHCO$_3$/brine (1/1), and extracted with EtOAc. The combined organic layers were washed with brine and concentrated. The residue was purified by chromatography on silica gel using hexane/acetone (100/0 to 60/40, 10 min) to obtain example 6 as a white solid (71 mg, 50% yield). LC-MS observed M+1=538.34 (Calcd. 538.35).

To a solution of example 6 (35 mg, 0.06 mmol) in THF/MeOH/H$_2$O (3/1/1, 3 mL) at RT was added LiOH monohydrate (55 mg, 1.30 mmol). The reaction mixture was stirred overnight, then quenched with 1N HCl/brine (1/1), and extracted with EtOAc. The combined organic layers were washed with brine and concentrated. The residue was purified by chromatography on silica gel using DCM/MeOH (100/0 to 85/15, 10 min) to afford a product example 7 as a white solid (28 mg, 82% yield). LC-MS observed M−1=522.32 (Calcd. 522.33).

Example 8 and 9

Example 8

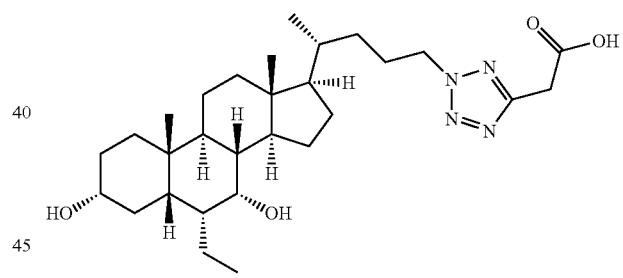

Example 7

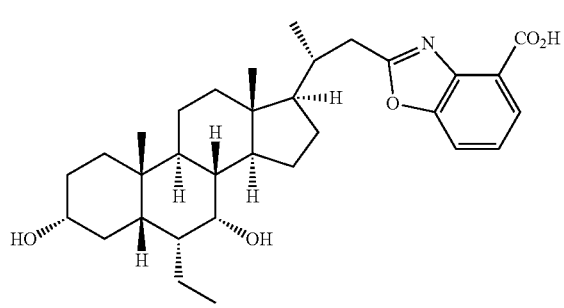

Example 6

LiOH →

Example 9

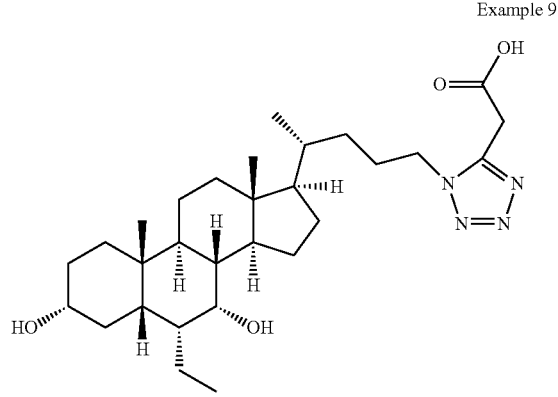

-continued

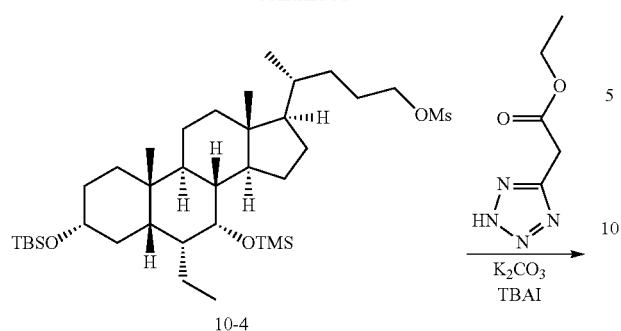

10-4

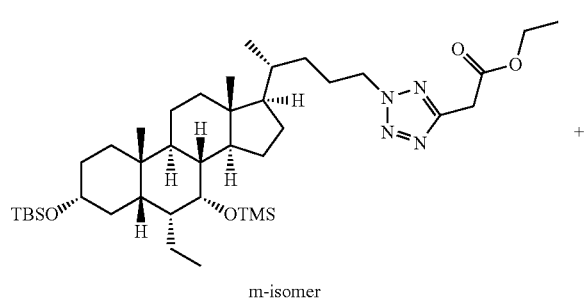

m-isomer

+

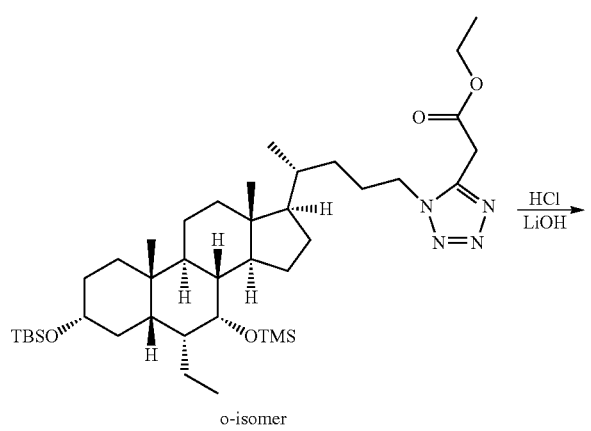

o-isomer $\xrightarrow{\text{HCl}}_{\text{LiOH}}$

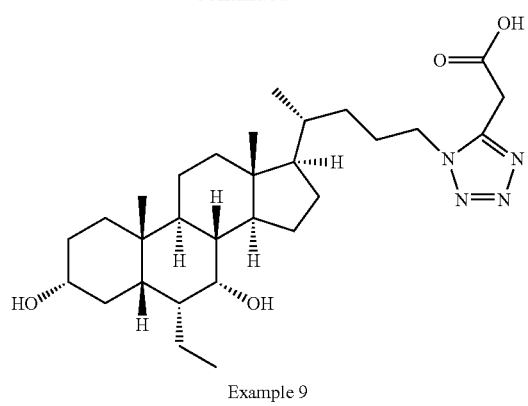

Example 9

To a solution of (10-4) (406 mg, 0.61 mmol) in DMF (7.6 mL) at RT was added ethyl 2-(2H-tetrazol-5-yl) acetate (189 mg, 1.21 mmol), K₂CO₃ (167 mg, 1.21 mmol) and TBAI (268 mg, 0.72 mmol). The reaction mixture was heated to 80° C. and stirred for 2 h, cooled to RT and diluted with 100 mL of EtOAc, and the organic layer was washed with water (50 mL) and brine (50 mL), then dried over Na₂SO₄. Filtration and concentration afforded crude residue, which was purified by chromatography on silica gel using hexane/EtOAc (100/0 to 50/50, 10 min) to provide two regioisomers as white solids (m-isomer, 300 mg, 68% yield; o-isomer, 135 mg, 30% yield), which were converted to example 8 (68 mg, 32% yield) and example 9 (76 mg, 82% yield) by deprotection of the silyl groups with HCl (37%) and hydrolysis of the ester group with LiOH following the same procedure as above (example 7). Example 8: LC-MS observed M−1=515.36 (Calcd. 515.37); example 9: LC-MS observed M−1=515.36 (Calcd. 515.37).

Example 10

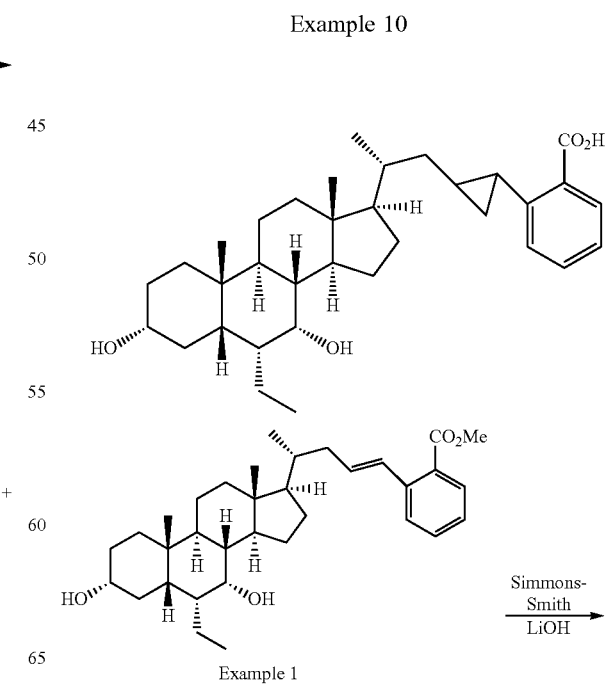

Example 1

$\xrightarrow[\text{LiOH}]{\text{Simmons-Smith}}$

Example 8

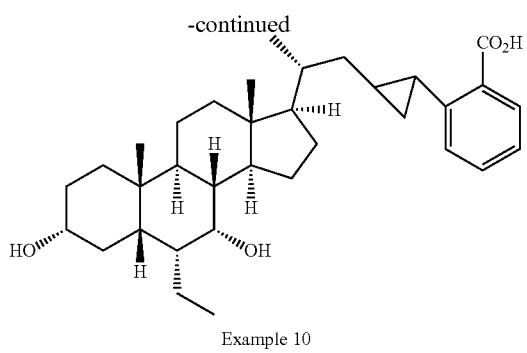

Example 10

To a solution of example 1 (53 mg, 0.1 mmol) in DCM (2 mL) at 0° C. under $N_2$ was added dropwise 1.0 M $Et_2Zn$ solution in hexane (0.5 mL), followed by dropwise addition of $CH_2I_2$ (41 µL, 0.5 mmol). The reaction mixture was stirred at 0° C. for 20 min, then allowed to warm up to RT, and stirred for another 4 h, quenched slowly with sat. $NH_4Cl$, and extracted with EtOAc. The combined organic layers were washed with brine and concentrated. The residue was purified by chromatography on silica gel using hexane/acetone (100/0 to 60/40, 10 min) to give a product as a white solid (37 mg, 70%). The product (27 mg, 0.05 mmol) was first dissolved in THF/MeOH/$H_2O$ (3/1/1, 2.5 mL) and treated with LiOH.$H_2O$ (43 mg, 1.02 mmol). The reaction mixture was stirred at RT for 2 d, then quenched with 1N HCl/brine (1/1), and extracted with EtOAc. The combined organic layers were concentrated and the residue was purified by chromatography on silica gel using hexane/acetone (100/0 to 50/50, 10 min) to give compound 10 as a white solid (22 mg, 84%). LC-MS observed 2M+1=1045.73 (Calcd. 1045.74).

Example 11

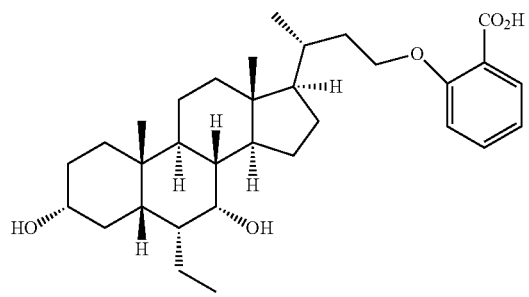

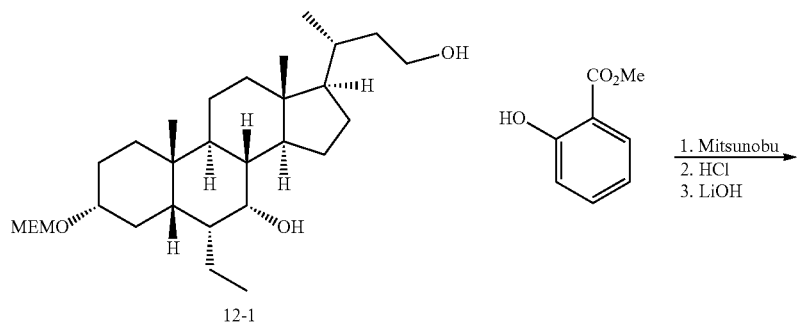

12-1

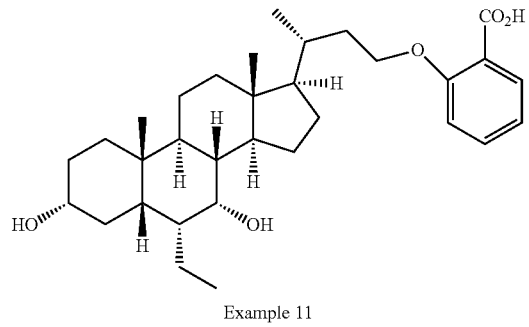

Example 11

To a stirred solution of methyl 2-hydroxybenzoate (Methyl salicylate) (0.128 ml, 0.998 mmol), 12-1 (240 mg, 0.5 mmol) and triphenylphosphine (262 mg, 0.998 mmol) in THF (3 mL) was added dropwise DEAD (0.158 mL, 0.998 mmol). The reaction mixture was stirred at RT overnight, quenched with brine, and extracted with EtOAc. The combined organic layers were washed with brine and concentrated. The residue was purified by chromatography on silica gel using hexane/EtOAc (100/0 to 55/45, 10 min) to afford a product as a colorless oil (212 mg, 69%), which was dissolved in THF (3 mL) and treated with 0.2 ml of 37% HCl. The mixture was stirred at RT for 2 h, quenched with 5% NaHCO$_3$ and brine (1/1), and extracted with EtOAc. The combined organic layers were washed with brine and concentrated. The residue was purified by chromatography on silica gel using hexane/EtOAc (100/0 to 60/40, 10 min) to give a product as a colorless oil (135 mg, 74%). LC-MS 2M+NH$_4$=1070.74 (calcd. 1070.77).

To a solution of the above methyl ester (65 mg, 0.123 mmol) in THF/MeOH/H$_2$O (3/1/1, 4 mL) was added LiOH.H$_2$O (104 mg, 2.468 mmol). The mixture was stirred at RT for 20 h, quenched with 1N HCl/brine (1/1), and extracted with EtOAc. The combined organic layers were concentrated and the residue was purified by chromatography on silica gel using DCM/MeOH (100/0 to 85/15, 10 min) to give a product as a white solid (50 mg, 79%). LC-MS 2M−1=1023.69 (calcd. 1023.70).

The following compounds (Table 1) were prepared from the corresponding alkene or halide intermediate according to the general procedures described for the preparation of Examples 1, 2 and 3.

TABLE 1

| Example | Structure | Physical data LC-MS |
|---|---|---|
| 12 | 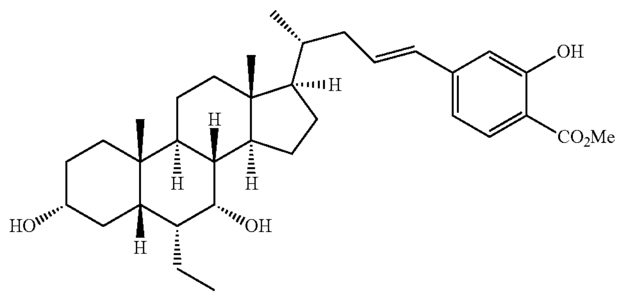 | 2M + 1 = 1077.74<br>Calcd. 1077.74 |
| 13 | 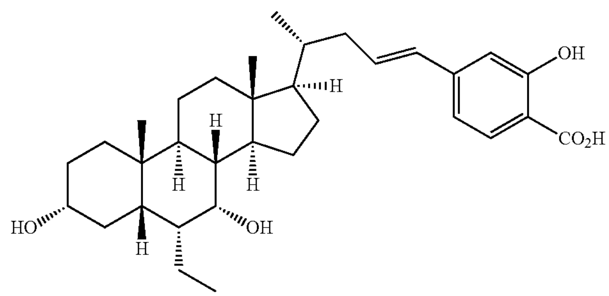 | M − 1 = 523.34<br>Calcd. 523.35 |
| 14 | 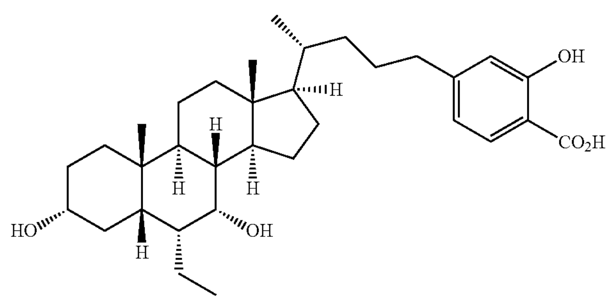 | M − 1 = 525.34<br>Calcd. 525.37 |
| 15 | 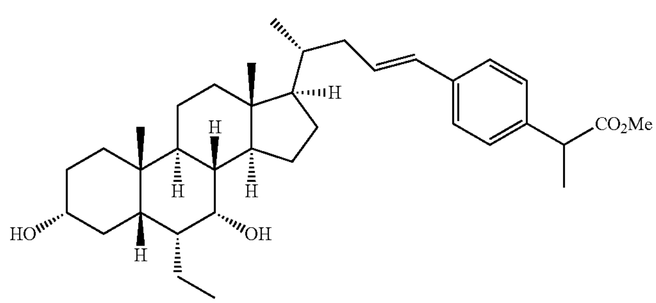 | M + NH$_4$ = 568.44<br>Calcd. 568.43 |

TABLE 1-continued

| Example | Structure | Physical data LC-MS |
|---|---|---|
| 16 | 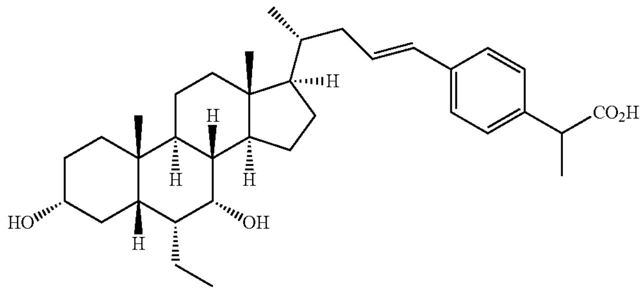 | M − 1 = 535.38<br>Calcd. 535.39 |
| 17 | 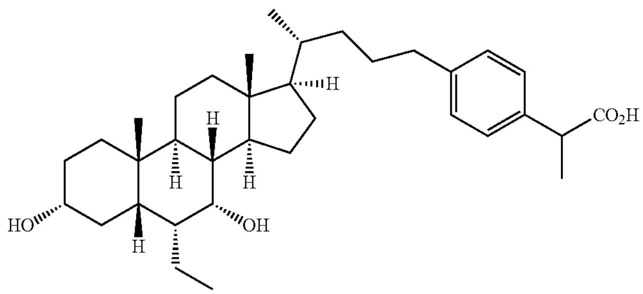 | M − 1 = 537.40<br>Calcd. 537.40 |
| 18 | 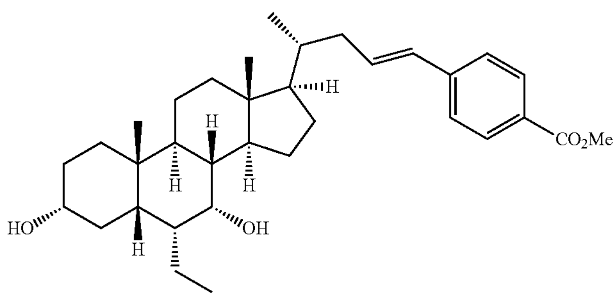 | 2M + 1 = 1045.75<br>Calcd. 1045.74 |
| 19 | 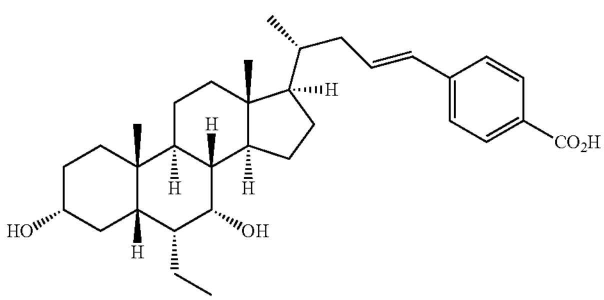 | M − 1 = 507.35<br>Calcd. 507.36 |
| 20 | 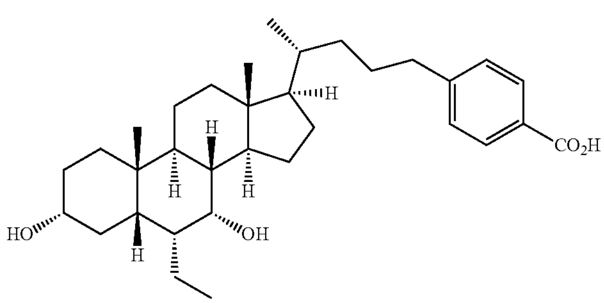 | M − 1 = 509.36<br>Calcd. 509.37 |

TABLE 1-continued

| Example | Structure | Physical data LC-MS |
|---|---|---|
| 21 | 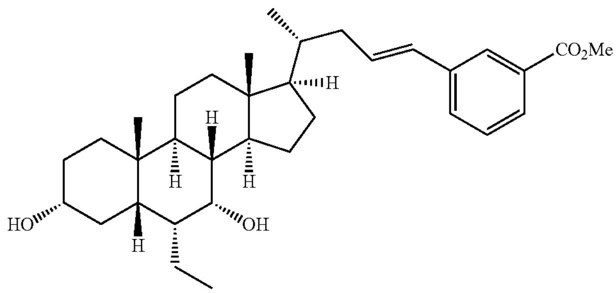 | 2M + NH₄ = 1062.78<br>Calcd. 1062.77 |
| 22 | 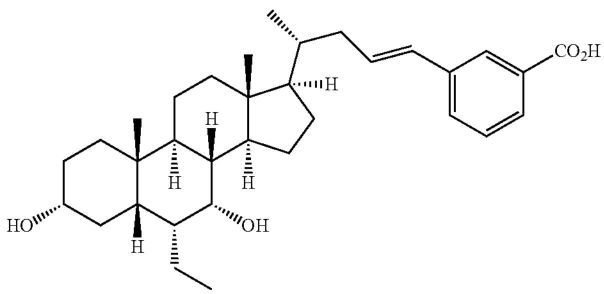 | M − 1 = 507.35<br>Calcd. 507.36 |
| 23 | 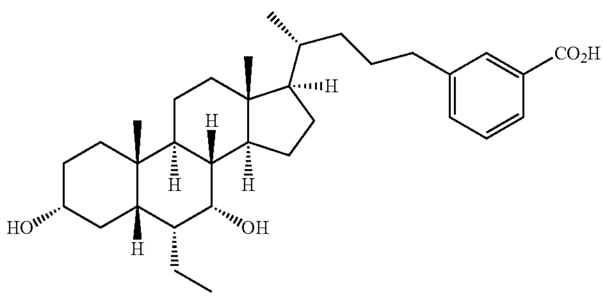 | M − 1 = 509.36<br>Calcd. 509.37 |
| 24 | 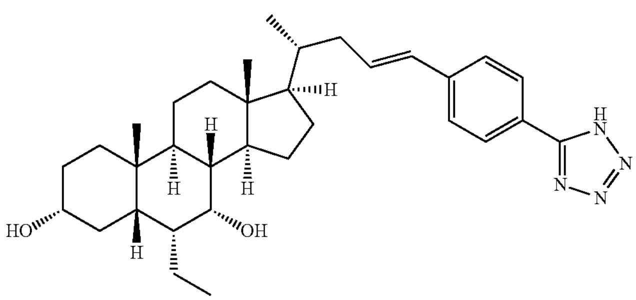 | 2M + 1 = 1065.74<br>Calcd. 1065.76 |
| 25 | 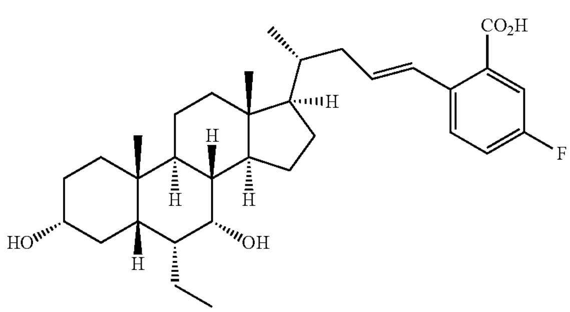 | 2M + NH₄ = 1070.69<br>Calcd. 1070.73 |

TABLE 1-continued

| Example | Structure | Physical data LC-MS |
|---|---|---|
| 26 | 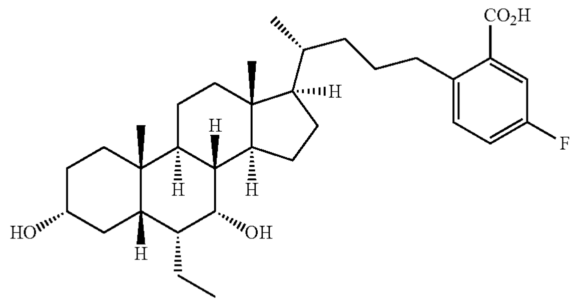 | M − 1 = 527.35<br>Calcd. 527.36 |
| 27 | 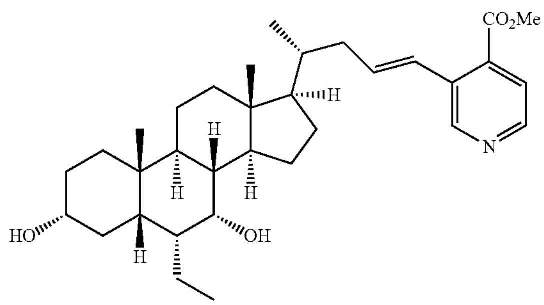 | M + 1 = 524.38<br>Calcd. 524.37 |
| 28 | 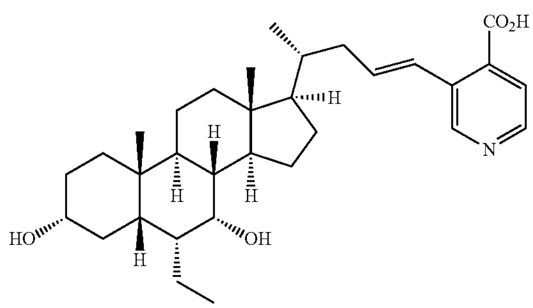 | M − 1 = 508.34<br>Calcd. 508.35 |
| 29 | 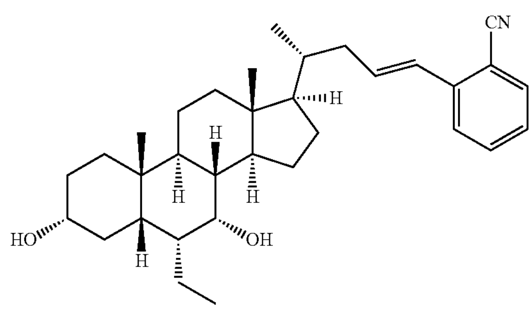 | 2M + NH$_4$ = 996.73<br>Calcd. 996.75 |
| 30 | 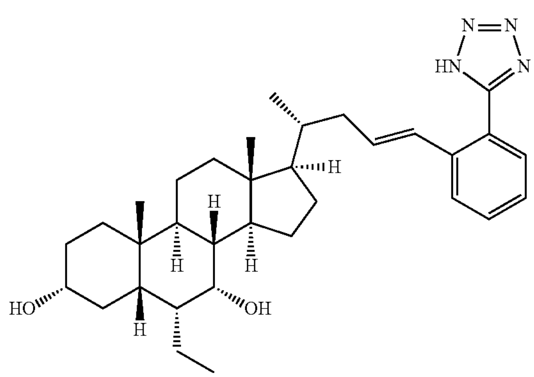 | M − 1 = 531.37<br>Calcd. 531.38 |

The following compounds (Table 2) were prepared using the general methods described in Examples 7, 10 and 11.

TABLE 2

| Example | Structure | Physical Data LC-MS |
|---|---|---|
| 31 | 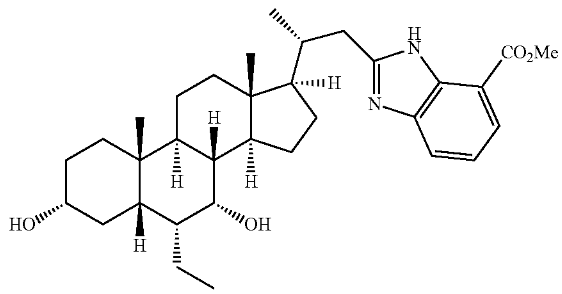 | M + 1 = 537.37<br>Calcd. 537.36 |
| 32 | 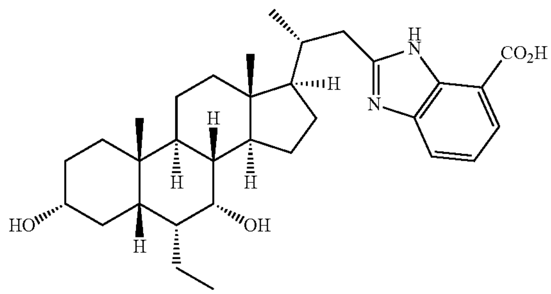 | M + $HCO_2H$ − 1 = 567.39<br>Calcd. 567.36 |
| 33 | 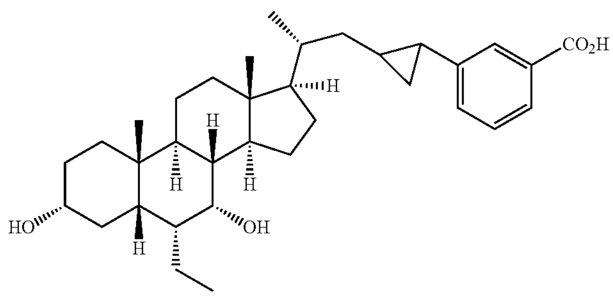 | M − 1 = 521.36<br>Calcd. 521.37 |
| 34 | 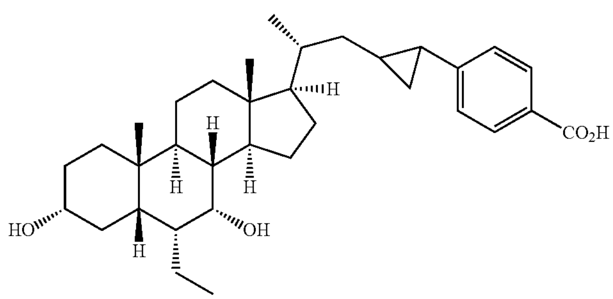 | M − 1 = 521.36<br>Calcd. 521.37 |
| 35 | 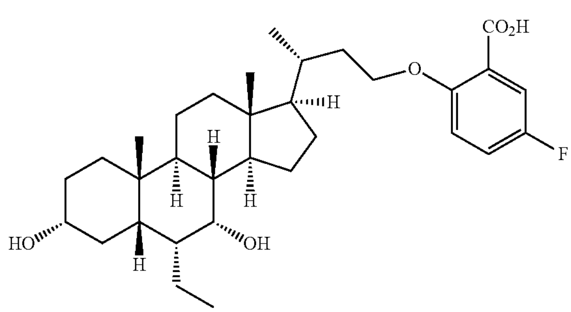 | 2M − 1 = 1059.67<br>Calcd. 1059.68 |

Assays
Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

In Vitro Human TGR5 (GPBAR1) Activity Assay

The potency and efficacy of the compounds of the invention on TGR5 receptor was evaluated using in vitro assays which carried out using the express kit from DiscoverX (cAMP HUNTER™ eXpress GPBAR1 CHO-K1 GPCR Assay; number: 95-0049E2CP2S). GPBAR1 (G protein-coupled bile acid receptor 1) encodes a member of the G protein-coupled receptor (GPCR) superfamily. GPBAR1 activation following ligand binding initiates a series of second messenger cascades that result in a cellular response. Treatment of CHO cells expressing GPBAR1 with induces the production of intracellular cAMP and internalization of the receptor. The potency and efficacy of compound for GPBAR1 activation by measuring cyclic adenosine monophosphate (cyclic AMP or cAMP) levels in live cells using a competitive immunoassay based on Enzyme Fragment Complementation (EFC). In brief, following seeding the cells into the white, 96 well microplate, place it in a 37° C., 5% $CO_2$ in a humidified incubator for 18-24 hours prior to testing. On second day, proceed to the appropriate cAMP HUNTER™ eXpress Protocol according to the manufacturer's instructions. Dissolve agonist compound in DMSO at the desired stock concentration, and prepare 3-fold serial dilutions of agonist compound in Cell Assay Buffer. The concentration of each dilution should be prepared at 4× of the final screening concentration (i.e., 15 μL compound+45 μL Cell Assay Buffer/cAMP Antibody Reagent). For each dilution, the final concentration of solvent should remain constant. Transfer 15 μL diluted compound the assay plate and incubate the plate for 30 minutes at 37° C. Following agonist incubation, add 60 μL of working cAMP detection reagents/cAMP Solution mixture (cAMP Lysis Buffer, Substrate Reagent 1, cAMP Solution D) to the appropriate wells. Incubate for 1 hour at room temperature (23° C.), protected from light. Add 60 μl of cAMP Solution A to the appropriate wells. Incubate for 3 hours at room temperature (23° C.), protected from light. Read samples on Envision standard luminescence plate reader. Calculate of average $EC_{50}$ after logarithm transformation.

To assess the FXR agonistic potency of the example compounds as well as for reference compound, potency ranges were determined in the Human FXR (NR1H4) Assay as listed below in Table 3. The efficacy was normalized to CDCA set as 100%. (A: EC50<0.1 μM; B: 0.1 μM<EC50<1.0 μM; C: 1.0 μM<EC50<10 μM; D: EC50>10 μM).

TABLE 3

| Example | EC50 (μM) | Efficacy (%) |
| --- | --- | --- |
| CDCA | D | 100 |
| 6-ECDCA | B | 239 |
| 1 | C | 217 |
| 2 | A | 313 |
| 3 | B | 352 |
| 4 | B | 298 |
| 5 | C | 271 |
| 6 | C | 131 |
| 7 | B | 195 |
| 8 | C | 29 |
| 9 | C | 172 |
| 10 | B | 252 |
| 11 | B | 388 |
| 12 | C | 134 |
| 13 | B | 166 |
| 14 | C | 232 |
| 15 | C | 40 |
| 16 | C | 248 |
| 17 | C | 261 |
| 18 | C | 113 |
| 19 | B | 244 |
| 20 | C | 266 |
| 21 | C | 92 |
| 22 | C | 195 |
| 23 | C | 292 |
| 24 | C | 234 |
| 25 | A | 376 |
| 26 | B | 256 |
| 27 | C | 296 |
| 28 | B | 300 |
| 29 | C | 210 |
| 30 | B | 332 |
| 31 | C | 34 |
| 32 | C | 24 |

TABLE 3-continued

| Example | EC50 (µM) | Efficacy (%) |
| --- | --- | --- |
| 33 | C | 229 |
| 34 | C | 195 |
| 35 | B | 203 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula I

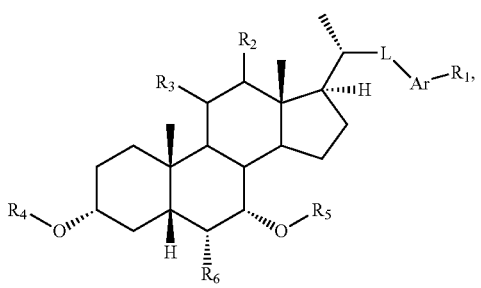

or a pharmaceutically acceptable salt or ester thereof, wherein:

—Ar—$R_1$ is selected from the groups set forth below, each of which is optionally substituted when possible:

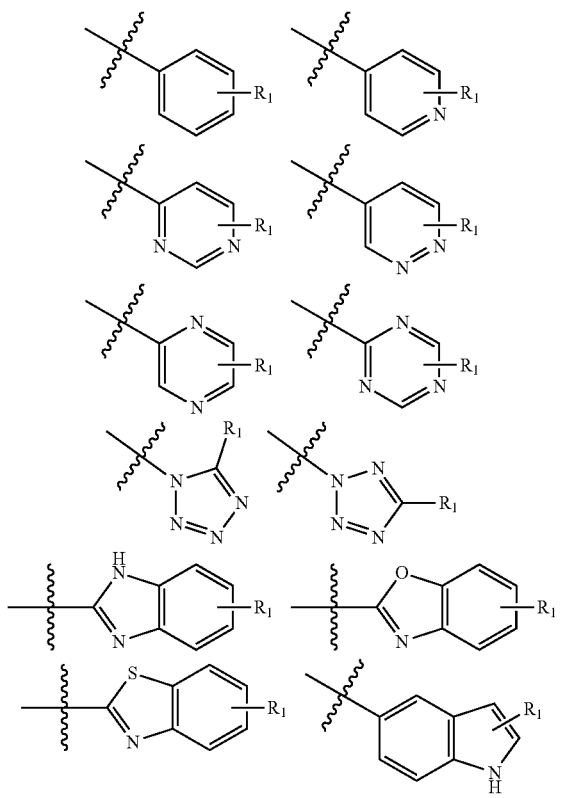

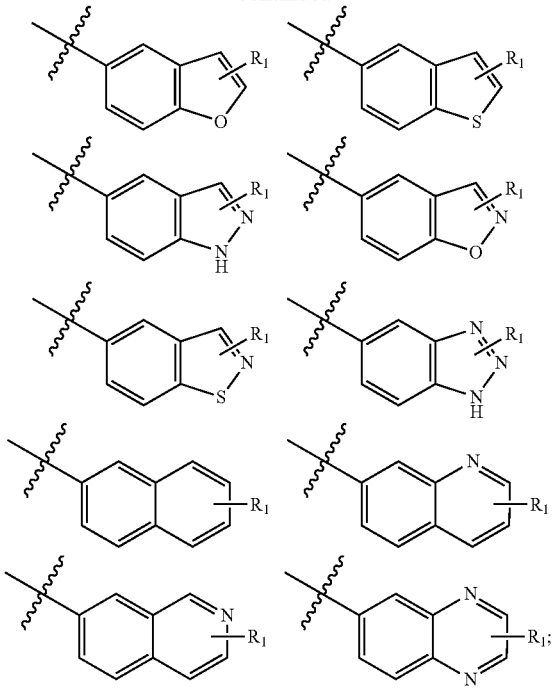

$R_1$ is —C(O)$R_{11}$; —C(O)N$R_{12}R_{13}$, —C(O)NHSO$_2R_{11}$, —P(O)($R_{11}$)$_2$, —CN, or tetrazolyl;

L is selected from the group consisting of:
  1) Substituted or unsubstituted —$C_1$-$C_8$-alkylene;
  2) Substituted or unsubstituted —$C_2$-$C_8$-alkenylene;
  3) Substituted or unsubstituted —$C_2$-$C_8$-alkynylene;
  4) Substituted or unsubstituted —$C_3$-$C_8$-cycloalkylene;
  5) Substituted or unsubstituted —$C_1$-$C_7$ alkoxylene;
  6) Substituted or unsubstituted —$C_1$-$C_7$ aminoalkylene;
  7) Substituted or unsubstituted —$C_3$-$C_7$ heterocycloalkylene;
  8) Substituted or unsubstituted —$C_1$-$C_8$-alkylene-$C_3$-$C_8$-cycloalkylene;
  9) Substituted or unsubstituted —$C_1$-$C_8$-alkylene-$C_3$-$C_7$-heterocycloalkylene;
  10) Substituted or unsubstituted alkylaryl; and
  11) Substituted or unsubstituted alkylheteroaryl;

$R_2$ is hydrogen, hydroxyl, halogen, —OSO$_3$H, —OSO$_3^-$, —OAc, —OPO$_3$H$_2$ or —OPO$_3^{2-}$;

$R_3$ is hydrogen, halogen, CN, N$_3$, hydroxyl, —OSO$_3$H, —OSO$_3^-$, —OAc, —OPO$_3$H$_2$, —OPO$_3^{2-}$, —S$R_{12}$ or —NH$R_{12}$;

alternatively, $R_2$ and $R_3$ are taken together with the carbon atoms to which they are attached to form —CH=CH—, cycloalkyl or heterocycloalkyl;

$R_4$ and $R_5$ are each independently hydrogen or a hydroxyl protecting group;

$R_6$ is ethyl;

$R_{11}$ at each occurrence is independently selected from the group consisting of:
  1) Hydrogen,
  2) Halogen;
  3) Hydroxyl;

4) Substituted or unsubstituted —C$_1$-C$_8$ alkoxy;

5) Substituted or unsubstituted —C$_1$-C$_8$ arylalkyl;

6) Substituted or unsubstituted —C$_2$-C$_8$ alkenyl;

7) Substituted or unsubstituted —C$_2$-C$_8$ heteroarylalkynyl;

8) Substituted or unsubstituted —C$_3$-C$_8$ cycloalkyl;

9) Substituted or unsubstituted —C$_3$-C$_8$ cycloalkenyl;

10) Substituted or unsubstituted 3- to 8-membered heterocycloalkyl;

11) Substituted or unsubstituted aryl;

12) Substituted or unsubstituted arylalkyl;

13) Substituted or unsubstituted heteroaryl; and

14) Substituted or unsubstituted heteroarylalkyl; and $R_{12}$ and $R_{13}$ are each independently selected from hydrogen, optionally substituted —C$_1$-C$_8$-alkyl, optionally substituted —C$_2$-C$_8$-alkenyl, optionally substituted —C$_2$-C$_8$-alkynyl; optionally substituted —C$_3$-C$_8$-cycloalkyl, optionally substituted 3- to 8-membered heterocyclic, optionally substituted aryl, optionally substituted arylalkyl, optionally substituted heteroaryl, and optionally substituted heteroarylalkyl;

alternatively, $R_{12}$ and $R_{13}$ are taken together with the nitrogen atom to which they are attached to form an optionally substituted heterocyclic ring.

2. The compound of claim 1, represented by Formula II,

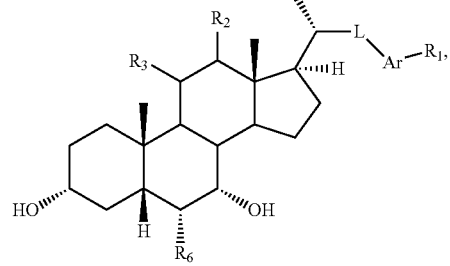

(II)

or a pharmaceutically acceptable salt or ester thereof, wherein $R_1$, Ar, L, $R_2$, $R_3$, and $R_6$ are as defined in claim 1.

3. The compound of claim 1, represented by Formula III,

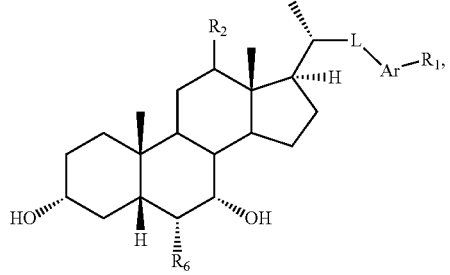

(III)

or a pharmaceutically acceptable salt or ester thereof, wherein $R_1$, Ar, L, $R_2$, and $R_6$ are as defined in claim 1.

4. The compound of claim 1, represented by Formula IV,

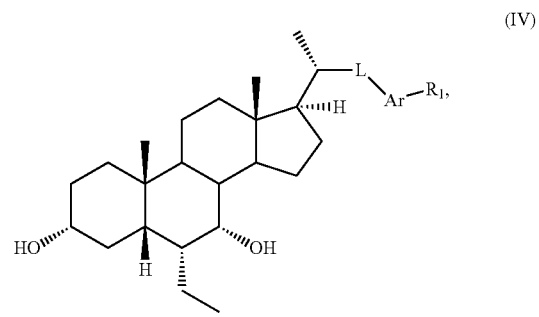

(IV)

or a pharmaceutically acceptable salt or ester thereof, wherein $R_1$, Ar and L are as defined in claim 1.

5. The compound of claim 1, wherein L is selected from the groups set forth below, each of which is optionally substituted:

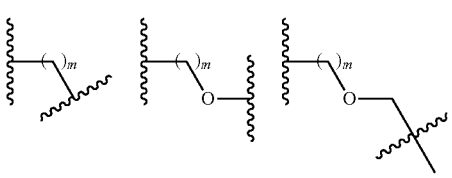

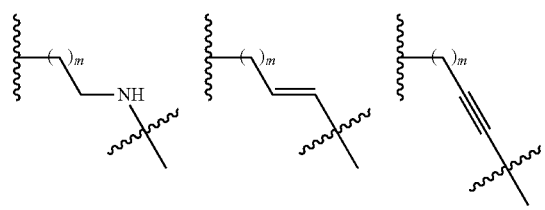

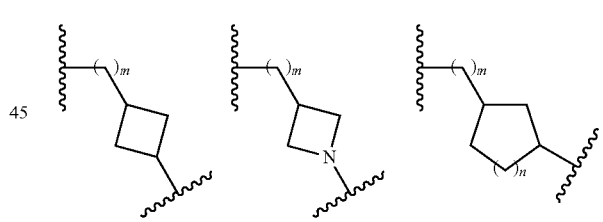

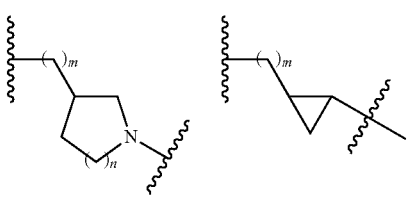

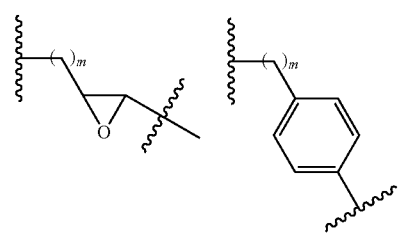

-continued
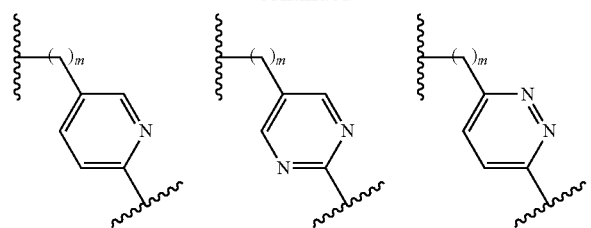
wherein m is 1, 2, 3, 4, 5, 6, or 7 and n is 1, 2, or 3.
6. A compound selected from compounds 1 to 42 below
Compound 1
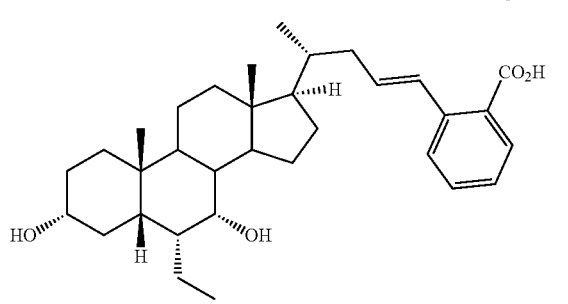
Compound 2
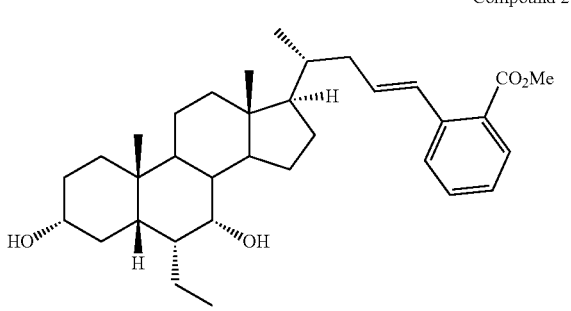
Compound 3
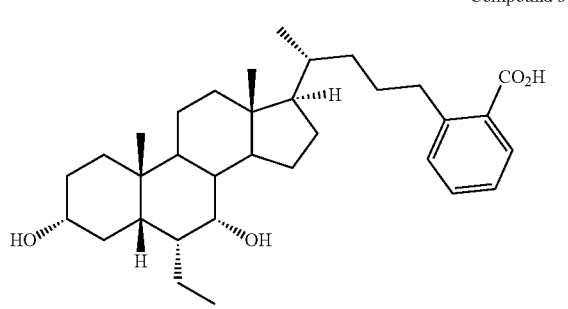
Compound 4
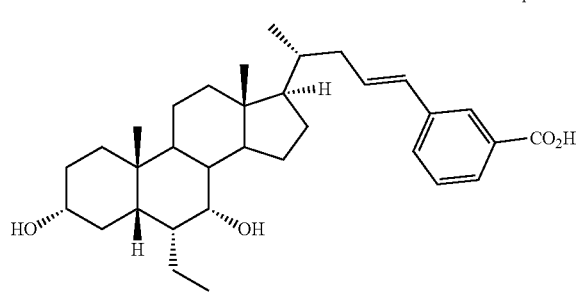
-continued
Compound 5
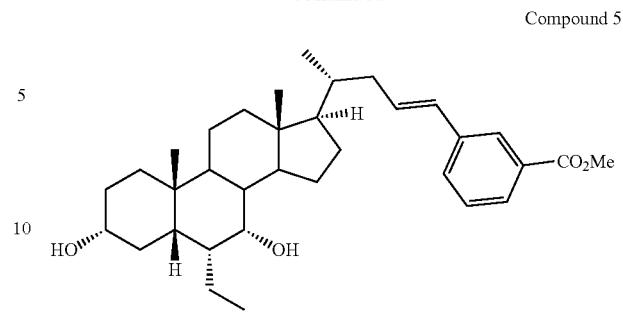
Compound 6
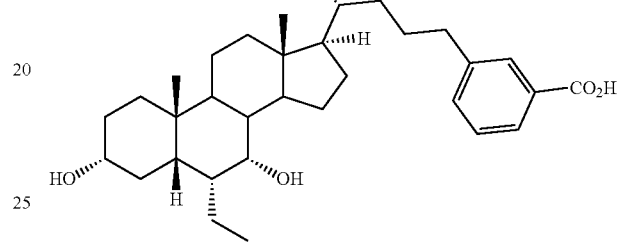
Compound 7
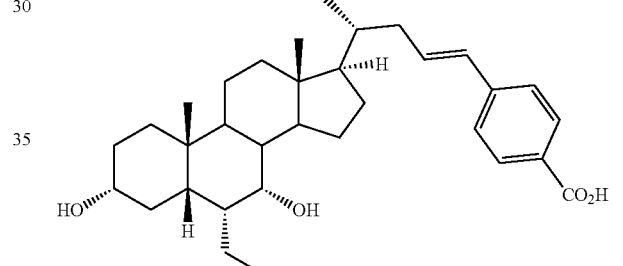
Compound 8
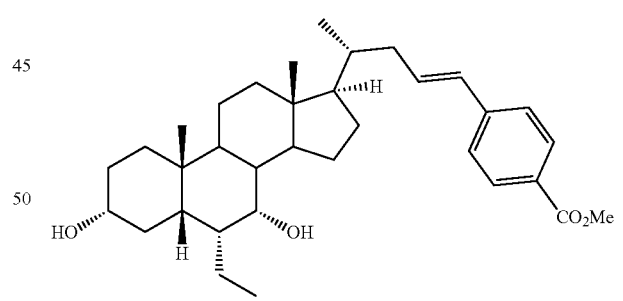
Compound 9
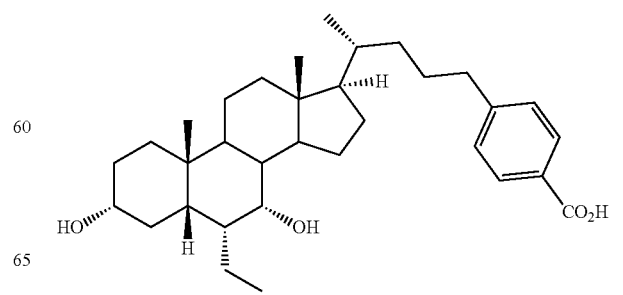

Compound 10
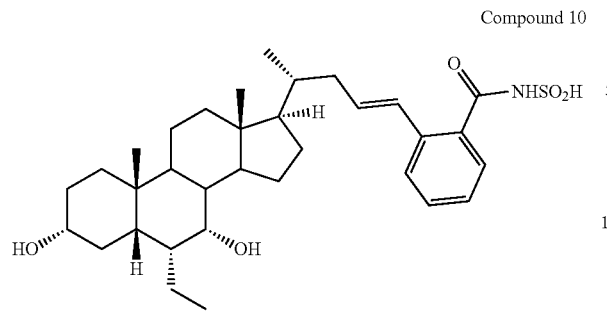
Compound 11
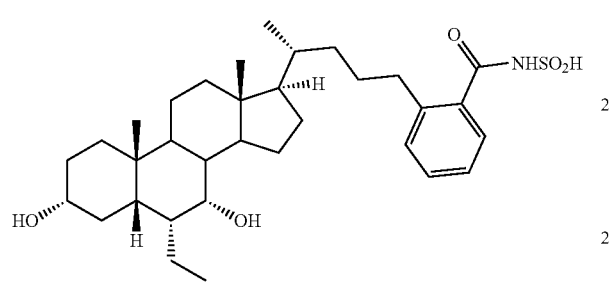
Compound 12
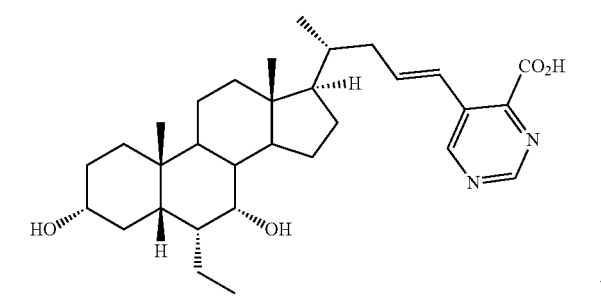
Compound 13
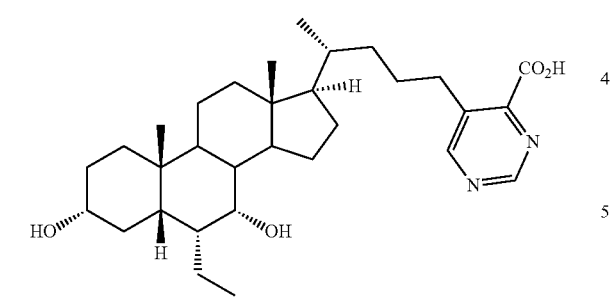
Compound 14
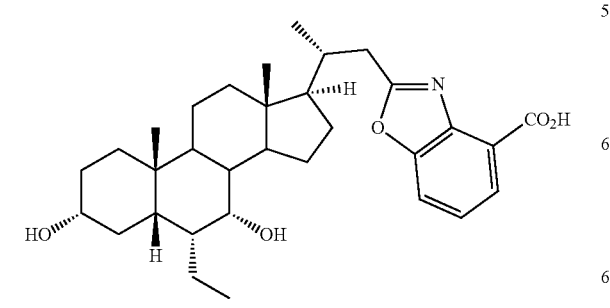
Compound 15
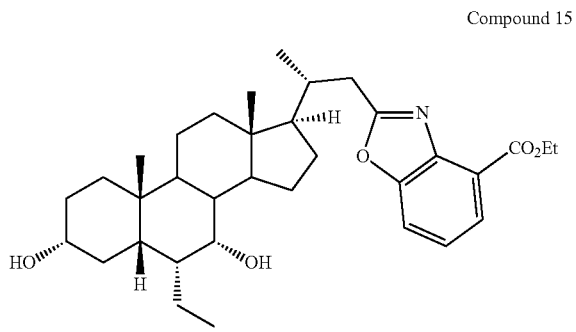
Compound 17
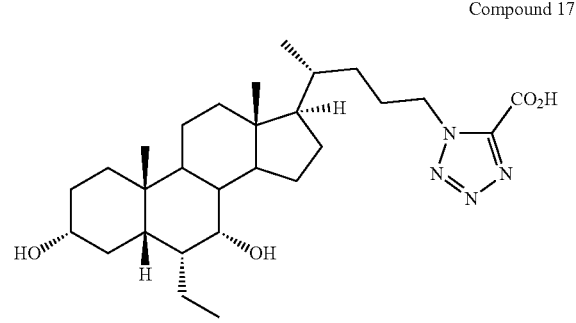
Compound 18
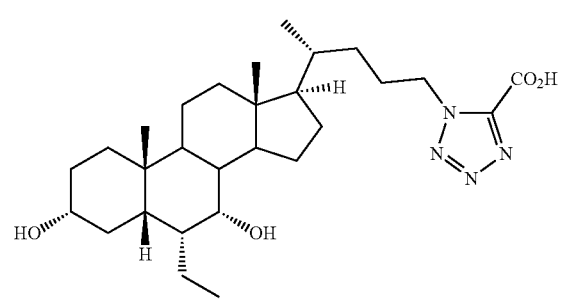
Compound 19
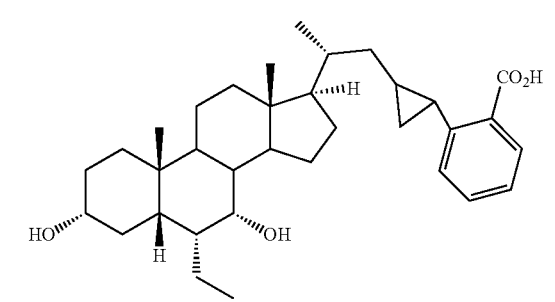
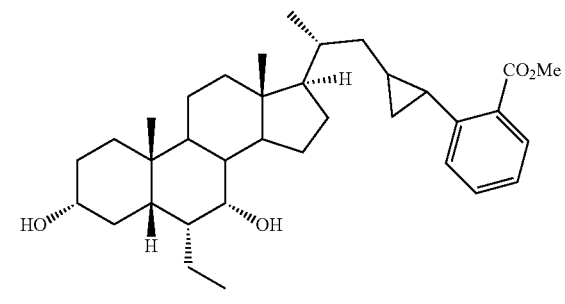

Compound 21
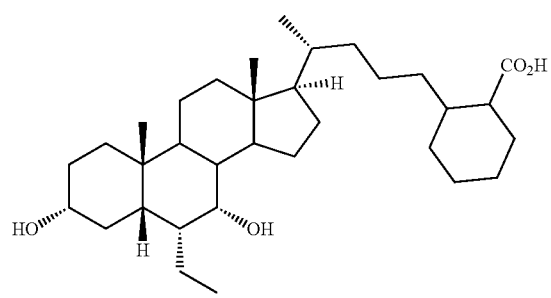
Compound 22
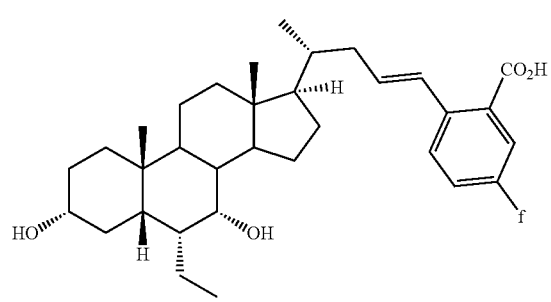
Compound 23
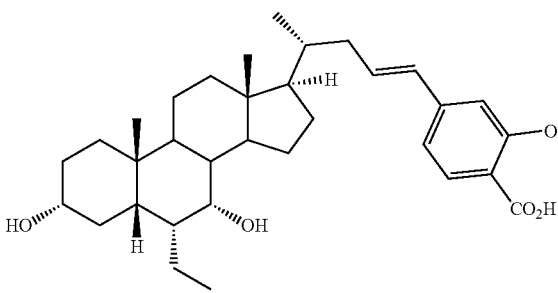
Compound 24
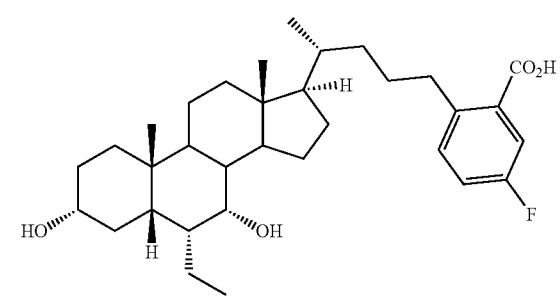
Compound 25
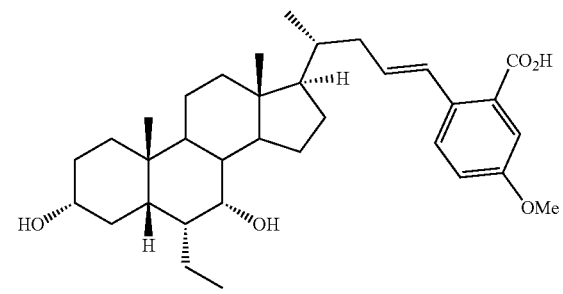
Compound 26
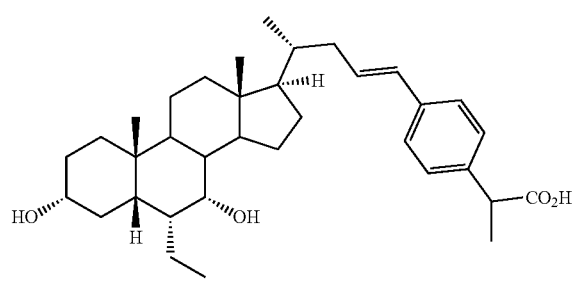
Compound 27
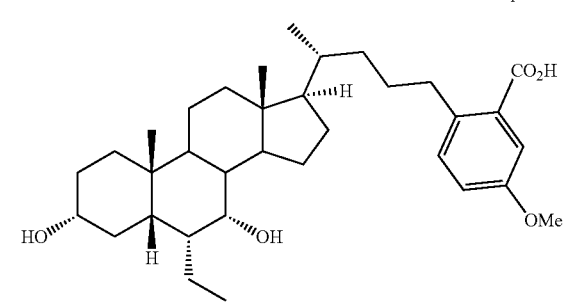
Compound 28
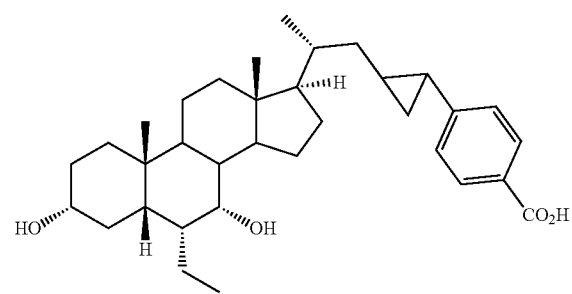
Compound 29
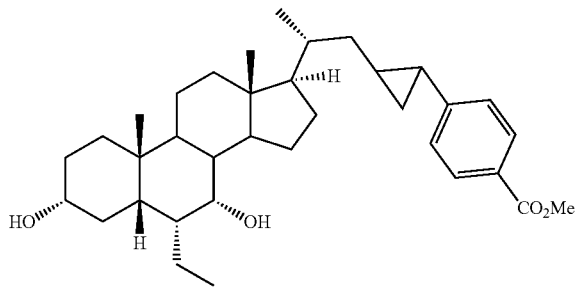
Compound 30
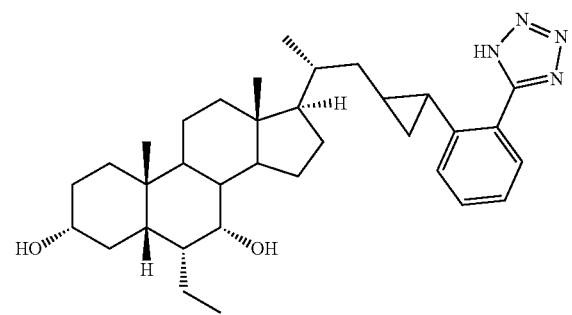

Compound 31
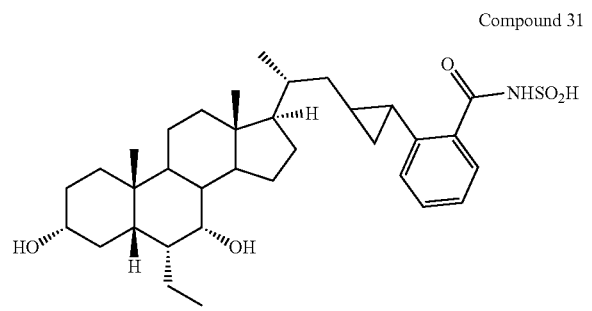
Compound 36
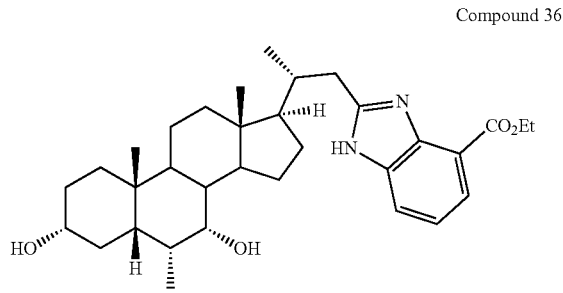
Compound 32
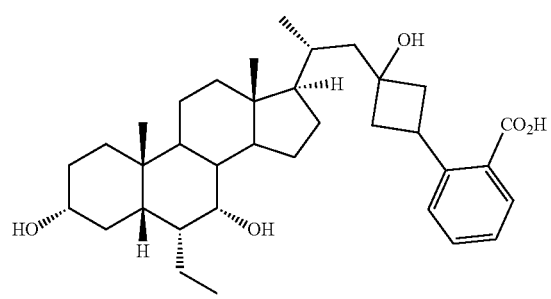
Compound 38
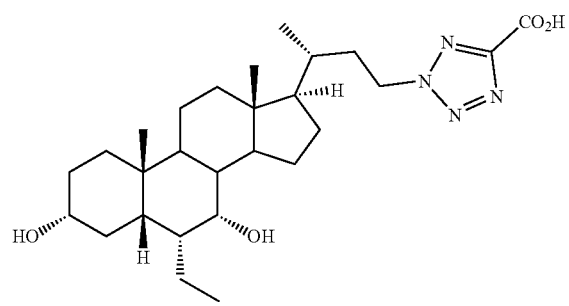
Compound 33
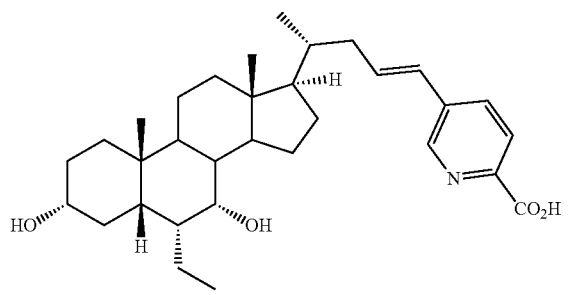
Compound 39
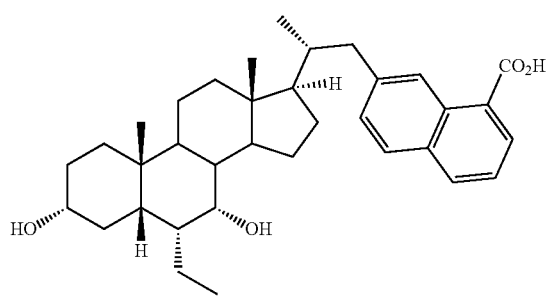
Compound 34
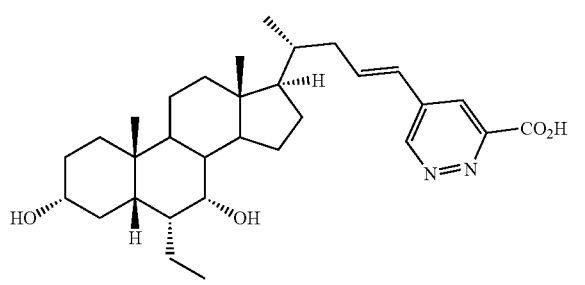
Compound 40
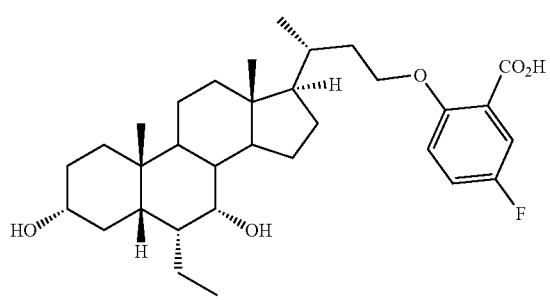
Compound 35
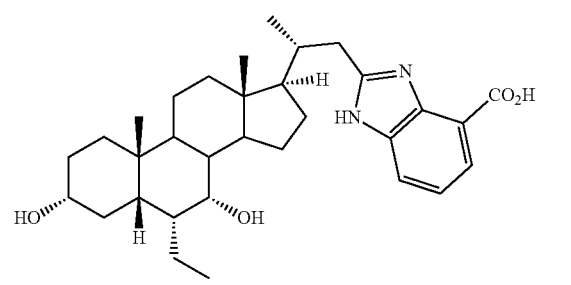
Compound 41
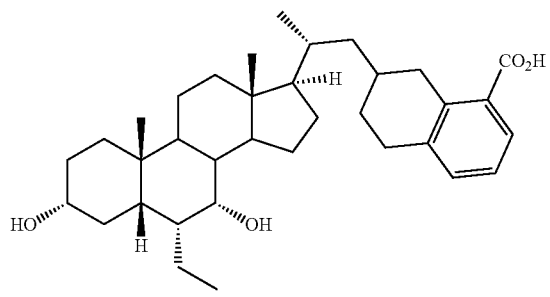

Compound 42
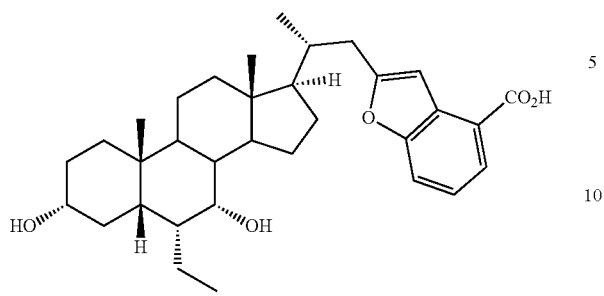
or a pharmaceutically acceptable salt or ester thereof.
7. A compound, selected from the compounds set forth below or a pharmaceutically acceptable salt or ester thereof:

-continued
| Compound | Structure |
|---|---|
| 7 | 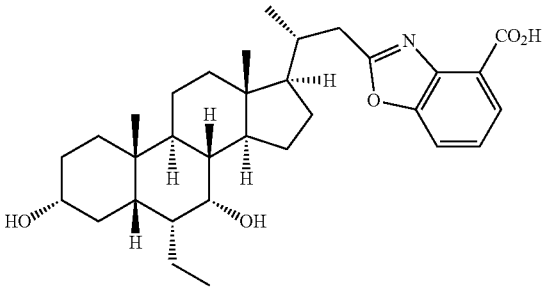 |
| 8 | 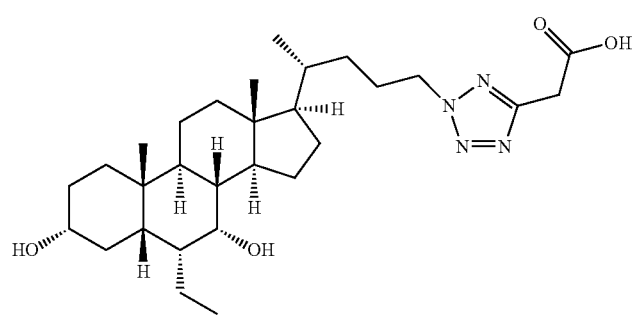 |
| 9 | 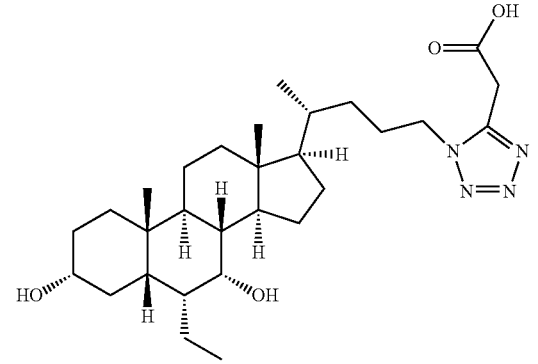 |
| 10 | 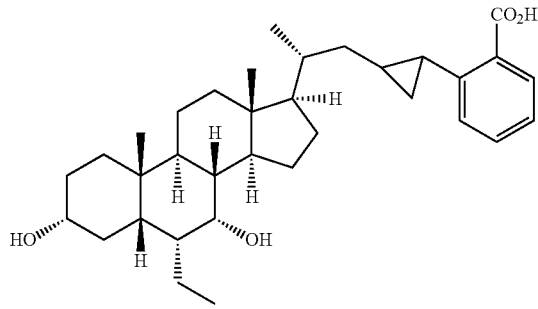 |
| 11 | 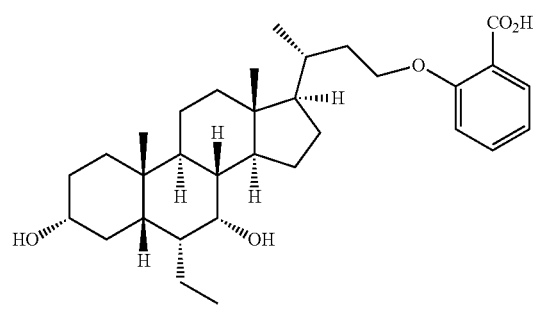 |

-continued

| Compound | Structure |
|---|---|
| 12 | 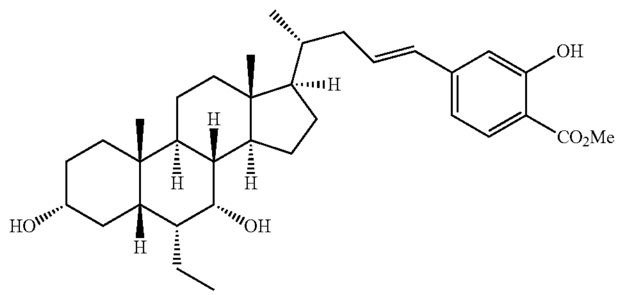 |
| 13 | 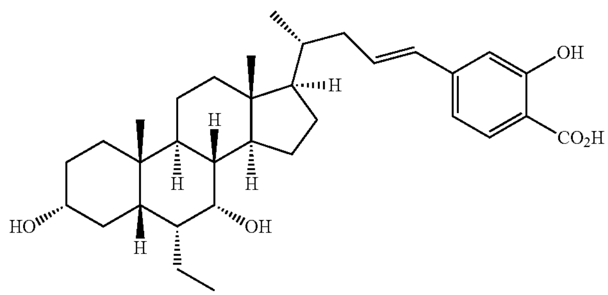 |
| 14 | 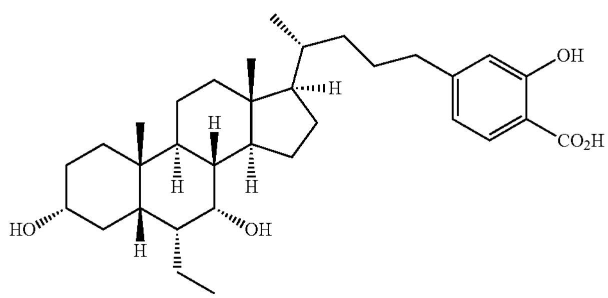 |
| 15 | 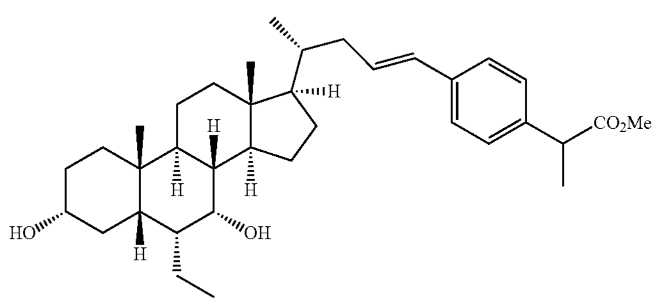 |
| 16 | 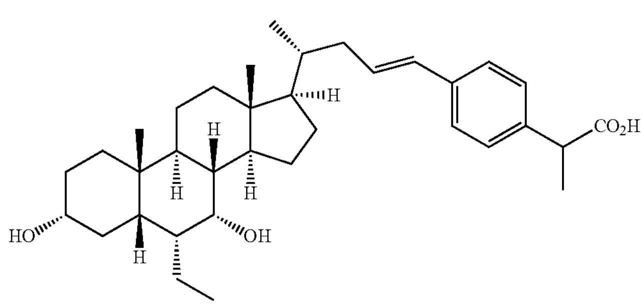 |

-continued
| Compound | Structure |
|---|---|
| 17 | 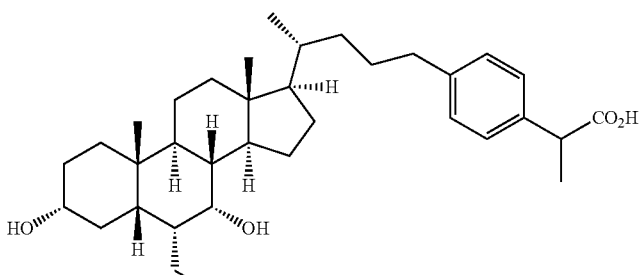 |
| 18 | 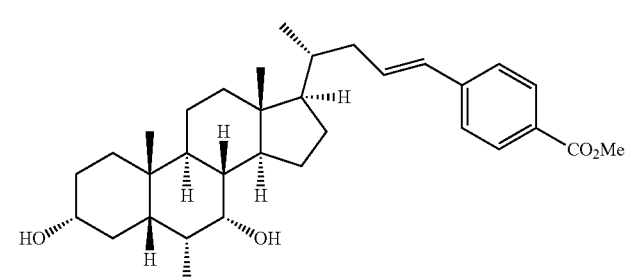 |
| 19 | 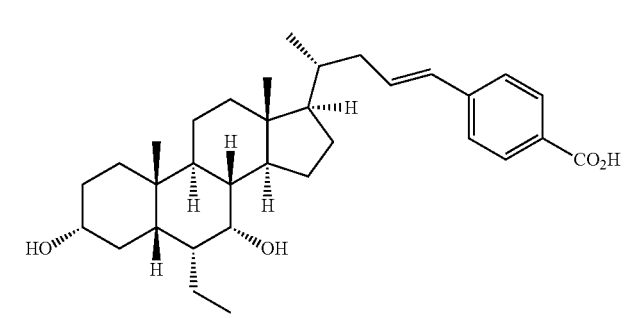 |
| 20 | 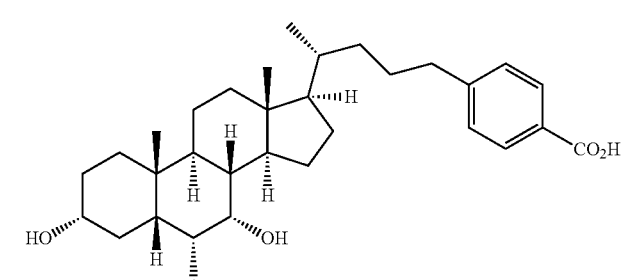 |
| 21 | 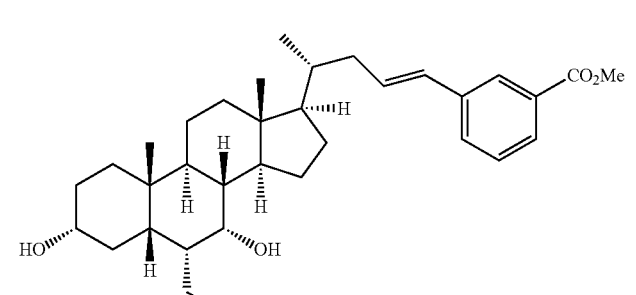 |

| Compound | Structure |
|---|---|
| 22 | (steroid with 3α-OH, 6α-ethyl, 7α-OH, side chain with trans-alkene to 3-carboxyphenyl) |
| 23 | (steroid with 3α-OH, 6α-ethyl, 7α-OH, side chain with propyl linker to 3-carboxyphenyl) |
| 24 | (steroid with 3α-OH, 6α-ethyl, 7α-OH, side chain with trans-alkene to 4-(1H-tetrazol-5-yl)phenyl) |
| 25 | (steroid with 3α-OH, 6α-ethyl, 7α-OH, side chain with trans-alkene to 2-carboxy-4-fluorophenyl) |
| 26 | (steroid with 3α-OH, 6α-ethyl, 7α-OH, side chain with propyl linker to 2-carboxy-4-fluorophenyl) |

-continued

| Compound | Structure |
|---|---|
| 27 | (steroid with 3α-OH, 6α-ethyl, 7α-OH, side chain with CH=CH-pyridine-CO₂Me) |
| 28 | (steroid with 3α-OH, 6α-ethyl, 7α-OH, side chain with CH=CH-pyridine-CO₂H) |
| 29 | (steroid with 3α-OH, 6α-ethyl, 7α-OH, side chain with CH=CH-phenyl-CN) |
| 30 | (steroid with 3α-OH, 6α-ethyl, 7α-OH, side chain with CH=CH-phenyl-tetrazole) |
| 31 | (steroid with 3α-OH, 6α-ethyl, 7α-OH, side chain with CH₂-benzimidazole-CO₂Me) |

-continued
| Compound | Structure |
|---|---|
| 32 | 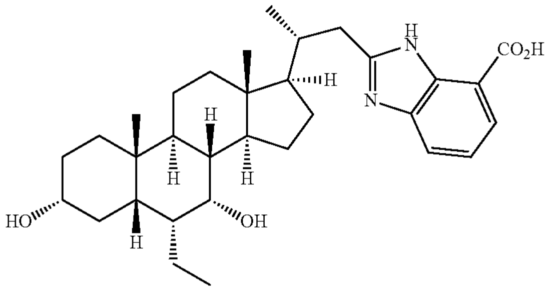 |
| 33 | 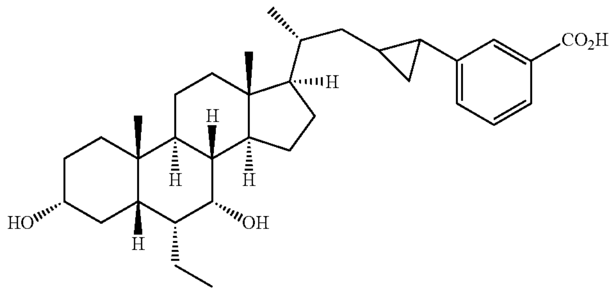 |
| 34 | 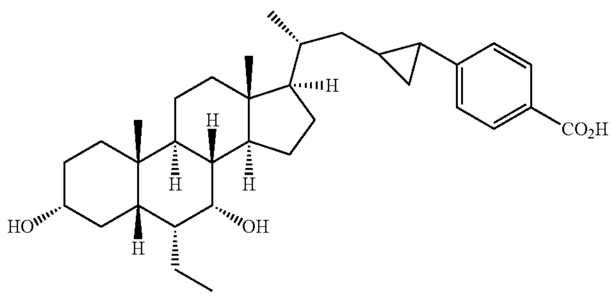 |
| 35 | 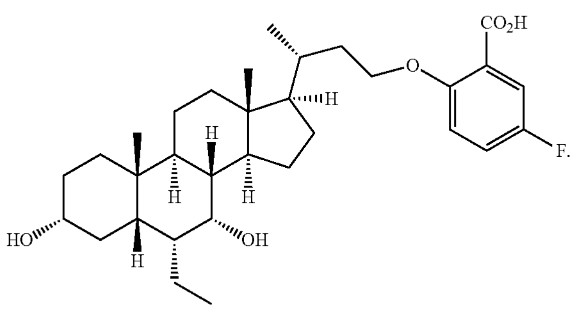 |
8. A pharmaceutical composition comprising a compound represented by Formula I,
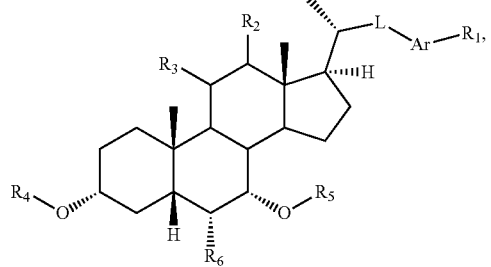
(I)
or a pharmaceutically acceptable salt or ester thereof, wherein:
—Ar—$R_1$ is selected from the groups set forth below, each of which is optionally substituted when possible:
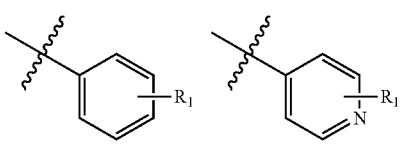

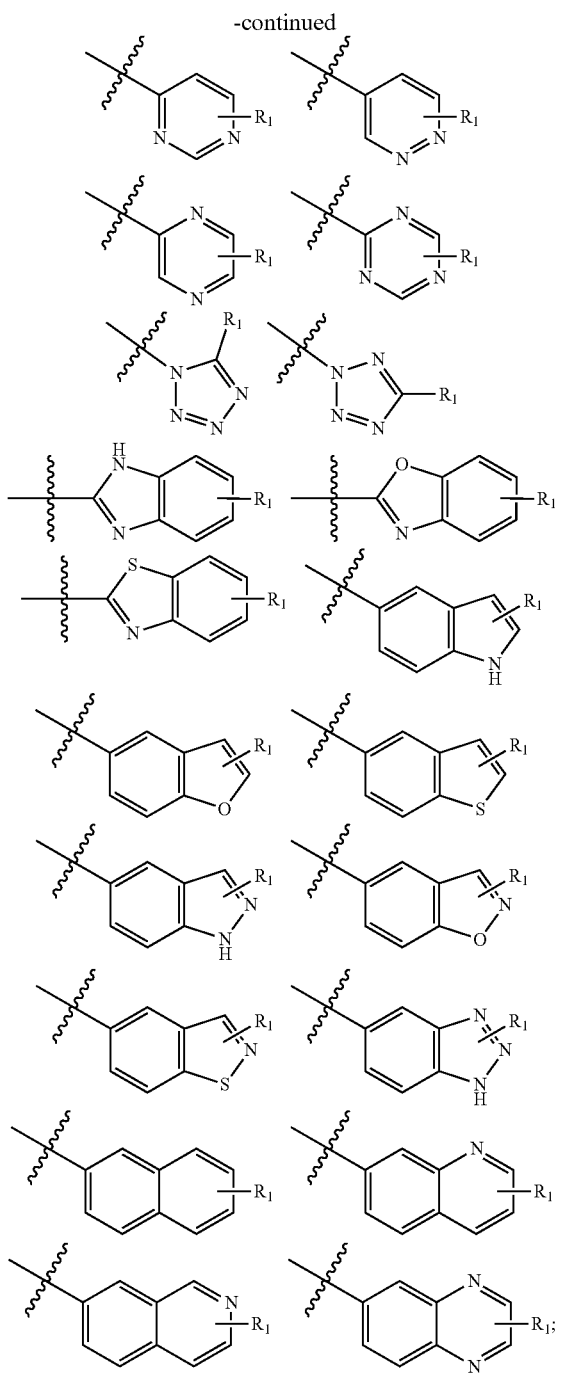

-continued $R_1$ is $-C(O)R_{11}$; $-C(O)NR_{12}R_{13}$, $-C(O)NHSO_2R_{11}$, $-P(O)(R_{11})_2$, $-CN$, or tetrazolyl;

L is selected from the group consisting of:
1) Substituted or unsubstituted $-C_1$-$C_8$-alkylene;
2) Substituted or unsubstituted $-C_2$-$C_8$-alkenylene;
3) Substituted or unsubstituted $-C_2$-$C_8$-alkynylene;
4) Substituted or unsubstituted $-C_3$-$C_8$-cycloalkylene;
5) Substituted or unsubstituted $-C_1$-$C_7$ alkoxylene;
6) Substituted or unsubstituted $-C_1$-$C_7$ aminoalkylene;
7) Substituted or unsubstituted $-C_3$-$C_7$ heterocycloalkylene;
8) Substituted or unsubstituted $-C_1$-$C_8$-alkylene-$C_3$-$C_8$-cycloalkylene;
9) Substituted or unsubstituted $-C_1$-$C_8$-alkylene-$C_3$-$C_7$-heterocycloalkylene;
10) Substituted or unsubstituted alkylaryl; and
11) Substituted or unsubstituted alkylheteroaryl;

$R_2$ is hydrogen, hydroxyl, halogen, $-OSO_3H$, $-OSO_3^-$, $-OAc$, $-OPO_3H_2$ or $-OPO_3^{2-}$;

$R_3$ is hydrogen, halogen, CN, $N_3$, hydroxyl, $-OSO_3H$, $-OSO_3-$, $-OAc$, $-OPO_3H_2$, $-OPO_3^{2-}$, $-SR_{12}$ or $-NHR_{12}$;

alternatively, $R_2$ and $R_3$ are taken together with the carbon atoms to which they are attached to form $-CH=CH-$, a cycloalkyl ring or a heterocycloalkyl ring;

$R_4$ and $R_5$ are each independently hydrogen or a hydroxyl protecting group;

$R_6$ is selected from the group consisting of:
1) Hydrogen;
2) Halogen;
3) Substituted or unsubstituted $-C_1$-$C_8$ alkyl;
4) Substituted or unsubstituted $-C_2$-$C_8$ alkenyl;
5) Substituted or unsubstituted $-C_2$-$C_8$ alkynyl;
6) Substituted or unsubstituted $-C_3$-$C_8$ cycloalkyl;
7) Substituted or unsubstituted $-C_1$-$C_7$ alkoxyl;
8) Substituted or unsubstituted $-C_1$-$C_7$ aminoalkyl; and
9) Substituted or unsubstituted $-C_3$-$C_7$ heterocycloalkyl;

R at each occurrence is independently selected from the group consisting of:
1) Hydrogen;
2) Halogen;
3) Hydroxyl;
4) Substituted or unsubstituted $-C_1$-$C_8$ alkoxy;
5) Substituted or unsubstituted $-C_1$-$C_8$ alkyl;
6) Substituted or unsubstituted $-C_2$-$C_8$ alkenyl;
7) Substituted or unsubstituted $-C_2$-$C_8$ alkynyl;
8) Substituted or unsubstituted $-C_3$-$C_8$ cycloalkyl;
9) Substituted or unsubstituted $-C_3$-$C_8$ cycloalkenyl;
10) Substituted or unsubstituted 3- to 8-membered heterocycloalkyl;
11) Substituted or unsubstituted aryl;
12) Substituted or unsubstituted arylalkyl;
13) Substituted or unsubstituted heteroaryl; and
14) Substituted or unsubstituted heteroarylalkyl; and $R_{12}$ and $R_{13}$ are each independently selected from hydrogen, optionally substituted $-C_1$-$C_8$-alkyl, optionally substituted $-C_2$-$C_8$-alkenyl, optionally substituted $-C_2$-$C_8$-alkynyl;

optionally substituted $-C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively, $R_{12}$ and $R_{13}$ are taken together with the nitrogen atom to which they are attached to form an optionally substituted heterocyclic ring; and a pharmaceutically acceptable carrier.

9. A method for ameliorating a disease or condition selected from the group consisting of primary biliary cirrhosis, cerebrotendinous xanthomatosis, primary sclerosing cholangitis, alcoholic liver disease, nonalcoholic fatty liver disease, nonalcoholic steatohepatitis, atherosclerosis, hypercholesterolemia, hypertriglyceridemia, Type II diabetes, and hepatocellular carcinoma in a subject in need thereof, comprising administering to the subject a therapeutically effective amount of the pharmaceutical composition of claim 8.

10. The method of claim 9, wherein the disease or condition is primary biliary cirrhosis.

11. The method of claim 9, wherein the disease or condition is nonalcoholic steatohepatitis.

12. The method of claim 9, wherein the disease or condition is nonalcoholic fatty liver disease.

\* \* \* \* \*